US006906024B1

(12) United States Patent
Baeck et al.

(10) Patent No.: US 6,906,024 B1
(45) Date of Patent: *Jun. 14, 2005

(54) FABRIC CARE COMPOSITIONS COMPRISING CELLULOSE BINDING DOMAINS

(75) Inventors: AndréCesar Baeck, Bonheiden (BE); Johan Smets, Lubbeek (BE); Stanton Lane Boyer, Fairfield, OH (US)

(73) Assignee: Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/674,477

(22) PCT Filed: Apr. 30, 1999

(86) PCT No.: PCT/US99/09410

§ 371 (c)(1), (2), (4) Date: Nov. 1, 2000

(87) PCT Pub. No.: WO99/57156

PCT Pub. Date: Nov. 11, 1999

(30) Foreign Application Priority Data

May 1, 1998 (WO) .............................. PCT/US98//08857

(51) Int. Cl.$^7$ ............................ C11D 3/00; C11D 7/18; C11D 7/54; C12N 9/00; C07K 1/00

(52) U.S. Cl. ........................ 510/515; 435/183; 435/193; 435/200; 536/23.2; 536/23.7; 530/350; 510/392; 510/305; 510/312; 510/276; 510/374

(58) Field of Search ............................... 435/4, 6, 69.1, 435/183, 193, 200, 252–253, 320.1, 325, 262, 263, 277; 536/23.2–23.7; 530/350; 510/392, 305, 312, 276, 374, 515, 114

(56) References Cited

U.S. PATENT DOCUMENTS

| | | | | |
|---|---|---|---|---|
| 6,410,498 B1 | * | 6/2002 | Smets et al. | 510/392 |
| 6,465,410 B1 | * | 10/2002 | Bettiol et al. | 510/392 |
| 6,468,955 B1 | * | 10/2002 | Smets et al. | 510/392 |

FOREIGN PATENT DOCUMENTS

| | | | | |
|---|---|---|---|---|
| WO | WO 93/05226 | | 3/1993 | D06M/16/00 |
| WO | WO 94/07998 | | 4/1994 | C12N/9/42 |
| WO | WO 94/21281 | * | 9/1994 | |
| WO | WO 97/01629 | | 1/1997 | C12N/9/42 |
| WO | WO 97/14804 | | 4/1997 | C12N/15/56 |
| WO | WO 98/00500 | | 1/1998 | C11D/3/386 |
| WO | WO 98/28411 | | 7/1998 | C12N/9/42 |

OTHER PUBLICATIONS

Goldstein et al. (J. Bacteriology, 1993, vol. 175(18):5762–5768).*

Sakka et al. (Ann NY Acad. Sci., Dec. 1998, vol. 864:485–488).*

Sigma Catalog, 1992, p. 634.*

Linder et al. Characterization of a double cellulose binding domain, J. Biol. Sci. vol. 271(35): 21268–21272. (1996).

* cited by examiner

*Primary Examiner*—Manjunath N. Rao
(74) *Attorney, Agent, or Firm*—C. Brant Cook; Kim W. Zerby; Steve W. Miller

(57) ABSTRACT

The present invention relates to fabric care compositions comprising one or more amino acid sequence(s) comprising a Cellulose Binding Domain for providing fabric care. In a further embodiment, the present invention relates to fabric care compositions wherein the amino acid sequence comprising one or more cellulose binding domains is linked to a softening protein.

6 Claims, No Drawings

FABRIC CARE COMPOSITIONS COMPRISING CELLULOSE BINDING DOMAINS

FIELD OF THE INVENTION

The present invention relates to fabric care compositions comprising an amino acid sequence comprising a Cellulose Binding Domain (CBD).

BACKGROUND OF THE INVENTION

Modern laundry detergent and/or fabric care compositions contain various detergent ingredients having one or more purposes in obtaining fabrics which are not only clean but also have retained appearance and integrity. Therefore, detergent components such as perfumes, soil release agents, fabric brightening agents, fabric softeners, chelants, bleaching agents and catalysts, dye fixatives and enzymes, have been incorporated in laundry detergent and/or fabric care compositions. One of such specific example is the use of enzymes, especially proteases, lipases, amylases and/or cellulases.

In particular, cellulase enzymes are used in detergent/fabric care compositions for their cleaning and fabric care benefits. The activity of cellulase is one in which cellulosic fibres or substrates are hydrolised by the cellulase and is depending on the particular function of the cellulase, which can be endo- or exo-cellulase, and on the respective hemicellulases. The cellulose structures are depolymerized or cleaved into smaller and thereby more soluble or dispersible fractions. This activity in particular on fabrics provides a cleaning, rejuvenating, softening and generally improved handfeel characteristics to the fabric structure. It is known in the art through protein analysis that cellobiohydrolases, major endoglucanases and bacterial cellulases posses a bifunctional organisation in the form of a catalytical core domain and a smaller cellulose binding domain separated by a linker or flexible hinge stretch of amino acids.

In recent years, consumer desirability for fabric conditioning compositions has risen. Fabric softening compositions impart several desirable properties to treated garments including softness and static control. Fabric softness of laundered garments is typically achieved by delivering a quaternary ammonium compound to the surface of the fabric. Consumer desirability for durable press fabric garments, particularly cotton fabric garments, has also risen. Durable press garments include those garments which resist wrinkling of the fabric both during wear and during the laundering process. Durable press garments can greatly decrease the hand work associated with laundering by eliminating ironing sometimes necessary to prevent wrinkling of the garment. However, in most commercially available durable press fabrics, the fabric's ability to resist wrinkling is reduced over time as the garment is repeatedly worn and laundered. Furthermore, coloured garments have a tendency to wear and show appearance losses. A portion of this colour loss may be attributed to abrasion in the laundering process, particularly in automatic washing machines and automatic laundry dryers. Moreover, tensile strength loss of fabric appears as an unavoidable result of mechanical/chemical action due to use/wearing or washing.

As indicated above, there is a continuous need for a fabric care composition, which can provide fabric softness and provide, refurbish or restore tensile strength, anti-wrinkle, anti-bobbling and anti-shrinkage properties to fabrics, as well as provide static control, colour appearance and fabric anti-wear properties and benefits.

The above objective has been met by formulating fabric care compositions comprising one or more amino acid sequence(s) comprising a Cellulose Binding Domain (CBD).

Enzymes linked to Cellulose Binding Domains are described in the art: WO 91/10732 novel derivatives of cellulase enzymes combining a core region derived from an endoglucanase producible by a strain of Bacillus spp., NICMB 40250 with a CBD derived from another cellulase enzyme or a combining a core region derived from another cellulase enzyme with a CBD derived from said endoglucanase, for improved binding properties. WO94/07998 describes cellulase variants of a cellulase classified in family 45, comprising a CBD, a Catalytically Active Domain (CAD) and a region linking the CBD to the CAD, wherein one or more amino acid residues have been added, deleted or substituted and/or another CBD is added at the opposite end of the CAD. WO95/16782 relates to the cloning and high level expression of novel truncated cellulase proteins or derivatives thereof in *Trichoderma longibrachiatum* comprising different core regions with several CBDs. WO97101629 describes cellulolytic enzyme preparation wherein the mobility of the cellulase component may be reduced by adsorption to an insoluble or soluble carrier e.g. via the existing or newly introduced CBD. WO97/28243 describes a process for removal or bleaching or soiling or stains from cellulosic fabrics wherein the fabric is contacted in aqueous medium with a modified enzyme which comprises a catalytically active amino acid sequence of a non-cellulolytic enzyme selected from amylases, proteases, lipases, pectinases and oxidoreductases, linked to an amino acid sequence comprising a cellulose binding domain and a detergent composition comprising such modified enzyme and a surfactant.

However, none of these documents disclose fabric care compositions comprising one or more amino acid sequence(s) comprising one or more Cellulose Binding Domain, for fabric care benefits.

SUMMARY OF THE INVENTION

The present invention relates to fabric care compositions comprising one or more amino acid sequence(s) comprising one or more cellulose binding domain, providing fabric care.

In a further embodiment, the present invention relates to fabric care compositions wherein the amino acid sequence comprising a cellulose binding domain, is linked to a softening protein.

The fabric care compositions of the present invention can further comprise a softening ingredient selected from cationic surfactants, a transferase enzyme and/or clays.

DETAILED DESCRIPTION OF THE INVENTION

An essential element of the fabric care compositions of the present invention is an amino acid sequence comprising a cellulose binding domain. This amino acid sequence comprising a cellulose binding domain (CBD) can be a naturally occurring sequence or can be modified : encompassed are cross-linked CBDs, i.e. amino acid sequences comprising a cellulose binding domain which are cross-linked to each other and/or CBDs further linked to a softening protein, i.e. an amino acid sequence comprising a cellulose binding domain linked to a softening protein.

Indeed, the present invention encompasses several embodiments:

In a first embodiment, the present invention relates to a fabric care composition comprising one or more amino acid sequence(s) comprising a cellulose binding domain. It has been surprisingly found that such compositions comprising one or more CBDs, provide softening, abrasion resistance and pilling prevention. Indeed, without wishing to be bound by theory, it is believed that the CBDs adsorb on the fibres of the fabric. Such adsorbed CBDs protect the fabric's fibers and thereby prevent the fibrillation of the cellulosic fibres. Moreover, CBDs are proteins and therefore provide softening.

In a second embodiment, the present invention encompasses a fabric care composition comprising cross-linked amino acid sequences comprising a cellulose binding domain. It has been surprisingly found that such cross-linked CBDs provide softness, prevent the fibrillation of cellulosic fibers as indicated above and also restore tensile strength, prevent the apparition of wrinkles, and increase the hydrophilicity of synthetic fibers. Indeed, without wishing to be bound by theory, it is believed that each cross-linked CBD can adsorb at opposite sites of the damaged fibers and thereby can restore tensile strength. Moreover, In a third embodiment, the present invention relates to a fabric care composition comprising the above describe embodiments which are further linked to a softening protein. Without wishing to be bound by theory, it is believed that the addition of a cellulose binding domain to a softening protein, allows a higher concentration of the softening protein onto the fabric, i.e. a closer and/or more lasting contact, resulting in a more efficient activity. Such modified softening proteins have an increased affinity (relative to unmodified softening protein) for binding to a cellulosic fabric or textile.

The above described fabric care composition may further comprise a softening ingredient selected from cationic surfactants, a transferase enzyme and/or clays.

Cellulose Binding Domain (CBD)

In the present context, the terms "amino acid sequence comprising a CBD or Cellulose Binding Domain or CBD" are intended to indicate an amino acid sequence capable of effecting binding of the cellulase to a cellulosic substrate (e.g. as described in P. Kraulis et al., Determination of the three-dimensional structure of the C terminal domain of cellobiohydrolase I from Trichoderma reesei. A study using nuclear magnetic resonance and hybrid distance geometry-dynamically simulated annealing. Biochemistry 28:7241–7257, 1989). The classification and properties of cellulose binding domains are presented in P. Tomme et al., in the symposium "Enzymatic degradation of insoluble polysaccharides" (ACS Symposium Series 618, edited by J. N. Saddler and M. H. Penner, ACS, 1995).

Cellulose-binding (and other carbohydrate-binding) domains are polypeptide amino acid sequences which occur as integral parts of large polypeptides or proteins consisting of two or more polypeptide amino acid sequence regions, especially in hydrolytic enzymes (hydrolases) which typically comprise a catalytic domain containing the active site for substrate hydrolysis and a carbohydrate-binding domain for binding to the carbohydrate substrate in question. Such enzymes can comprise more than one catalytic domain and one, two or three carbohydrate-binding domains, and they may further comprise one or more polypeptide amino acid sequence regions linking the carbohydrate-binding domain (s) with the catalytic domain(s), a region of the latter type usually being denoted a "linker".

Examples of hydrolytic enzymes comprising a cellulose-binding domain are cellulase, xylanases, mannanases, arabinofuranosidases, acetylesterases and chitinases. "Cellulose-binding domains" have also been found in algae, e.g. in the red alga porphyra purpurea in the form of a non-hydrolytic polysaccharide-binding protein [see P. Tomme et al., *Cellulose-binding domains—Classification* and *Properties in Enzymatic Degradation of Insoluble Carbohydrates*, John N. Saddler and Michael H. Penner (Eds.), ACS Symposium Series, No. 618 (1996)]. However, most of the known CBDs (which are classified and referred to by P. Tomme et al. (op. cit.) as "cellulose-binding domains"] derive from cellulases and xylanases.

In the present context, the term "cellulose-binding domain" is intended to be understood in the same manner as in the latter reference (P. Tomme et al., op. cit.) The P. Tomme et al. reference classifies more than 120 "cellulose-binding domains" into 10 families (I–X) which may have different functions or roles in connection with the mechanism of substrate binding. However, it is to be anticipated that new family representatives and additional families will appear in the future.

In proteins/polypeptides in which CBDs occur (e.g. enzymes, typically hydrolytic enzymes such as cellulases), a CBD may be located at the N or C terminus or at an internal position.

The part of a polypeptide or protein (e.g. hydrolytic enzyme) which constitutes a CBD per se typically consists of more than about 30 and less than about 250 amino acid residues. For example, those CBDs listed and classified in Family I in accordance with P. Tomme et al. (op. cit.) consist of 33–37 amino acid residues, those listed and classified in Family IIa consist of 95–108 amino acid residues, those listed and classified in Family VI consist of 85–92 amino acid residues, whilst one CBD (derived from a cellulase from Clostridium thermocellum) listed and classified in Family VII consists of 240 amino acid residues. Accordingly, the molecular weight of an amino acid sequence constituting a CBD per se will typically be in the range of from about 4 kD to about 40 kD, and usually below about 35 kD.

Cellulose binding domains can be produced by recombinant techniques as described in H. Stålbrand et al., Applied and Environmental Microbiology, Mar. 1995, pp. 1090–1097; E. Brun et al., (1995) Eur. J. Biochem. 231, pp. 142–148; J. B. Coutinho et al., (1992) Molecular Microbiology 6(9), pp. 1243–1252

In order to isolate a cellulose binding domain of, e.g. a cellulase, several genetic engineering approaches may be used. One method uses restriction enzyme to remove a portion of the gene and then to fuse the remaining gene-vector fragment in frame to obtain a mutated gene that encodes a protein truncated for a particular gene fragment. Another method involves the use of exonucleases such as Ba131to systematically delete nucleotides either externally from the 5' and the 3' ends of the DNA or internally from a restricted gap within the gene. These gene-deletion methods result in a mutated gene encoding a shortened gene molecule whose expression product may then be evaluated for substrate-binding (e.g. cellulose-binding) ability. Appropriate substrates for evaluating the binding ability include cellulosic materials such as Avicel™ and cotton fibres. Other methods include the use of a selective or specific protease capable of cleaving a CBD, e.g. a terminal CBD, from the remainder of the polypeptide chain of the protein in question.

Once a nucleotide sequence encoding the substrate-binding (carbohydrate-binding) region has been identified, either as cDNA or chromosomal DNA, it may then be manipulated in a variety of ways to fuse it to a DNA sequence encoding the amino acid sequence of interest. The DNA fragment encoding the carbohydrate-binding amino acid sequence, and the DNA encoding the amino acid sequence of interest are then ligated with or without a linker. The resulting ligated DNA may then be manipulated in a variety of ways to achieve expression. Preferred microbial expression hosts include certain *Aspergillus* species (e.g. *A. niger* or *A. oryzae*), *Bacillus* species, and organisms such as *Escherichia coli* or *Saccharomyces cerevisiae.*

Preferred CBDs for the purpose of the present invention are selected from the group consisting of: CBDs CBHII from *Trichoderma reesei*, CBDs CenC, CenA and Cex from *Cellulomonas fimi*, CBD CBHI from *Trichoderma reesei*, CBD Cellulozome from *Clostridium cellulovorans*, CBD E3 from *Thermonospora fusca*, CBD-dimer from *Clostridium stecorarium* (NCIMB11754) XynA, CBD from *Bacillus agaradherens* (NCIMB40482) and/or CBD family 45 from *Humicola insolens.* More preferred CBD for the purpose of the present invention are the CBD CenC from *Cellulomonas fimi,* CBD Cellulozome from *Clostridium cellulovorans* and/or the CBD originating from the fungal *Humicola Insolens* cellulase sold under the tradename "Carezyme" by Novo Nordisk A/S. Carezyme is an endoglucanase from family 45, derived from *Humicola insolens* DSM1800, having a molecular weight of about 43 kDa and exhibiting cellulolytic activity The fabric care composition can comprise one or more of the above described CBDs, any of these CBDs which are cross linked and/or further linked to a softening protein and/or mixtures thereof. The cross-linked CBDs of the present invention can comprise the amino acid sequence comprising from 2 to 50, preferably 2 to 10 cellulose binding domains. The CBDs comprised in the fabric care compositions of the present invention may originate from different sources. The CBDs, the cross-linked CBDs and/or the CBD linked to a softening protein are generally comprised in the fabric care compositions of the present invention at a level of from 0.01% to 10% and preferably from 0.1% to 6% and in a concentrated fabric care composition, from 0.2% to 30%, from 2% to 20% by weight.

For example, as described by M. Linder et al in The Journal of Biological Chemistry, Vol. 271, No. 35, Issue of August, pp 21268–21272, 1996, a double CBD by fusing the N-terminal CBD of *T. reesei* CBHII to the C-terminal CBD of CBHI by a linker region of 24 amino acids can be constructed. The linker region contains three amino acid residues from the natural CBHII linker followed by 21 amino acid residues from the natural CBHI linker. The double CBD was cloned an produced in *Escherichia coli.* It has been observed that the two domains interact during binding on cellulose, resulting in a higher binding affinity of the double CBD than either of the two single domains by themselves. Construction of the Double CBD Peptide—All DNA manipulations were performed using standard protocols. The gene constructions were first assembled into the vector pSP73 (Promega). The coding region for the pelB signal sequence of *Erwinia carotovora* was fused in frame with the coding region of the first 41 N-terminal residues of CBHII derived from the plasmid pTTc9, which in turn was linked to the coding region of the last 57 residues of CBHI derived from the plasmid pTTcl). For expression in *E. coli*, the construction was inserted into the expression vector pKK223-3, containing the isopropyl-β-D-thiogalactopyranoside-inducible tac promoter. The nucleotide sequence of the final construct was verified by sequencing.

Fermentation—The *E. coli* cultivations for producing the double CBD were carried out in a Chemap CMF laboratory fermenter with a working volume of 1.5 liters. A pH of 7 was maintained throughout the fermentation, and the rate of agitation was controlled to maintain constant dissolved oxygen levels. During the exponential growth phase (15–20 h after inoculation), isopropyl-β-D-thiogalactopyranoside was added to a final concentration of 0.5 mM to induce gene expression. The fermentation was continued until maximal levels of product had been reached (20–30 h).

Purification of the Double CBD—Culture supernatant was centrifuged (10.000 rpm, 45 min) and mixed with an equal volume of 20 mM phosphate buffer, pH 8.0, containing 1.5 M ammonium sulfate and kept at 4° C. overnight. Precipitation was removed by centrifugation as above, and the supernatant was filtered through a 0.45 μm Durapore (Millipore Corp.) membrane. The clarified supernatant was then loaded onto a butyl-Sepharose 4B column (Pharmacia Biotech Inc.) previously equilibrated with 10 mM phosphate buffer, pH 8.0, containing 0.75 M ammonium sulfate. The column was then washed with equilibration buffer, and the bound protein was eluted with 10 mM phosphate buffer, pH 8.0. The eluted peak fractions were loaded onto a Source RPC column (Pharmacia) equilibrated with Milli-Q water-:trifluoroacetic acid (1000:1). Bound peptide was eluted with an increasing linear gradient of acetonitrile:trifluoroacetic acid (1000:1). The purified peptide was then lyophilized. During all purification steps the double CBD was identified by the monoclonal antibody CI-89, which is specific toward the CBHI CBD. All chromatographic steps were run on a fast protein liquid chromatography (Pharmacia) system.

Proteolytic Cleavage—The lyophilized peptide was redissolved in 100 mM Tris buffer, pH 8.2 (2 mg/ml) and 10 units of immobilized trypsin (Sigma T-4019) added per mg of peptide. The suspension was incubated at 37° C. overnight, purified by the chromatography on Source RPC media (see above), and then lyophilized. The cleavage products were characterized and identified by amino acid analysis and MALDI-MS.

Analytical Techniques for the CBD Peptides—Purity control and quantification of CBD peptides was performed by RP-HPLC. A Pro-PepVydac C18 analytical column was used with gradient elution with water:trifluoroacetic acid (1000:1) to acetonitrile:trifluoroacetic acid (1000:1). Absorbance at 225 nm was used for detection. Quantification of peptide in the culture supernatant was also possible by this technique.

Production and Purification of the Double CBD—The amino acid sequence of the processed form of the double CBD is shown in FIG. 1 (M. Linder et al in The Journal of Biological Chemistry, Vol. 271, No. 35, Issue of August, pp 21268–21272, 1996). In fermentor cultivations of the *E. coli* WCM105 strain 60–80 mg/liter of the peptide was secreted into the culture medium, yielding 40–50 mg/liter of pure peptide (see FIG. 2—M. Linder et al in The Journal of Biological Chemistry, Vol. 271, No. 35, Issue of August, pp 21268–21272, 1996). The identity and correct processing of the peptide was verified by amino acid composition analysis. The peptide identity was also confirmed by Western blotting with a monoclonal antibody specific for the CBHI CBD.

The fabric care composition can also comprise the above described amino acid sequences further linked to a softening protein.

It has been found that enzyme proteins surprisingly show high adsorbability to a cellulosic fiber (EP 687 729). Enzyme proteins used in the present invention are those generically defined as a class of proteins having a particular structure for catalytic action. In other words, all proteins that possess a structure for catalytic action can be used, whether or not they exhibit catalytic action. However, enzyme proteins suitable for the purpose of the present invention are inactive. Inactivation can occur for example by inhibition, by the distortion of the three-dimensional structure for example by thermal or chemical means. When proteins other than enzyme proteins are used, the effects of the present invention may be obtained to some extent, but sufficient effect may not be achieved. Enzyme proteins have different biological origins: animal, plant and microbial origins. Enzyme proteins of any origin are usable for the present invention.

Such enzyme proteins, as classified on the basis of enzyme reaction type, include hydrolases, lyases, oxidoreductases, ligases, transferases and isomerases, all of which are usable for the present invention. A preference is given to hydrolases, exemplified by proteases (peptidase), glucosidases such as cellulase and amylase, and esterases such as lipase. The molecular weight of the enzyme protein is preferably not lower than 10,000, more preferably in the range of from 20,000 to 300,000. Being not lower than 10,000 in molecular weight, some enzyme proteins cannot penetrate the single fiber/monofilament (lamella structure) of cellulosic fibers such as a natural cellulose fiber and rayon. Also, they may not penetrate the monofilament of synthetic fibers, because the monofilament internal structure is dense. Enzyme adsorption sites of cellulosic fibers and synthetic fibers are therefore limited to the surface of the single fiber/monofilament.

Preferably the softening enzyme protein will be chosen from inactive enzyme comprising a CBD in nature, such as cellulase, xylanases, mannanases, arabinofuranosidases, acetylesterases and chitinases.

JP01280079 describes another type of softening proteins that can be used in the fabric care compositions of the present invention. These softening proteins are polyamino acid resin solution that adhere to synthetic, semi synthetic or cotton fabrics and thereby provide softness. These polyamino acids are preferably alpha amino acid such as glutamic acid, glycine, ornithine, mono- or co-polymer such as poly-gamma-L-glutamate.

Also suitable for the present invention are the C18 alkyl quaternary wheat protein derivatives sold under the tradename Coltide HQS by Croda Colloids Ltd. These wheat proteins derivatives generally included at levels of 0.04% to 0.2% by weight, are known to. provide great conditioning effect, i.e. to provide great handfeeling, softeness, to prevent fibres erosion of cotton and wool fabrics and to increase the lubricity of wool fibres.

Such amino acid sequence comprising one ore more CBDs and/or being further linked to a softening proteins (referred to as CBD hybrids and/or softening protein hybrids) can be prepared and purified by methods known in the art [see, e.g., WO 90/00609, WO 94/24158 and WO 95/16782, as well as Greenwood et al., *Biotechnology and Bioengineering* 44 (1994) pp. 1295–1305]. The production of enzymes hybrid is given in WO 91/10732 wherein novel derivatives of cellulase enzymes combining a core region derived from a *Bacillus* NICB 40250 endoglucanase with a CBD derived from another cellulase enzyme or a combining a core region derived from another cellulase enzyme with a CBD derived from a *Bacillus* NICB 40250 endoglucanase, are constructed. WO 95/16782 describes the combinations of different core regions with several CBD and the cloning and high level expression of these novel truncated cellulase proteins or derivatives thereof, in Trichoderma longibrachiatum.

The CBD hybrid and/or softening protein hybrid may, e.g., be prepared by transforming into a host cell a DNA construct comprising at least a fragment of DNA encoding the cellulose-binding domain ligated, with or without a linker, to a DNA sequence encoding the other cellulose binding domain and/or softening protein of interest, and growing the transformed host cell to express the fused gene. One relevant, but non-limiting, type of recombinant product (CBD hybrid and/or softening protein hybrid) obtainable in this matter—often referred to in the art as a "fusion protein"—may be described by one of the following general formulae:

A-CBD-MR-X-B

A-X-MR-CBD-B

In the latter formulae, CBD is an amino acid sequence comprising at least the cellulose-binding domain (CBD) per se.

MR (the middle region; a linking region) may be a bond, or a linking group comprising from 1 to about 100 amino acid residues, in particular of from 2 to 40 amino acid residues, e.g. from 2 to 15 amino acid residues. MR may, in principle, alternatively be a non-amino-acid linker (See below). X is an amino acid sequence comprising another cellulose binding domain and/or an amino acid sequence comprising the above-mentioned, inactive sequence of amino acid residues of a polypeptide encoded by a DNA sequence encoding the softening protein of interest.

The moieties A and B are independently optional. When present, a moiety A or B constitutes a terminal extension of a CBD or X moiety, and normally comprises one or more amino acid residues.

It will thus, inter alia, be apparent from the above that a CBD in a softening protein hybrid of the type in question may be positioned C-terminally, N-terminally or internally in the softening protein hybrid. Correspondingly, an X moiety in a softening protein hybrid of the type in question may be positioned N-terminally, C-terminally, or internally in the softening protein hybrid.

Softening protein hybrids of interest in the context of the invention include softening protein hybrids which comprise more than one CBD, e.g. such that two or more CBDs are linked directly to each other, or are separated from one another by means of spacer or linker sequences (consisting typically of a sequence of amino acid residues of appropriate length). Two CBDs in an softening protein hybrid of the type in question may, for example, also be separated from one another by means of an -MR-X- moiety as defined above. One or more cellulose binding domain can be linked to the N-terminal and/or C-terminal parts of the cellulase core region. Any part of a CBD can be selected, modified, truncated etc.

Preferably, attention will be paid in the construction of CBD hybrid and/or softening protein hybrids of the type in question to the stability towards proteolytic degradation. Two- and multi-domain proteins are particularly susceptible towards proteolytic cleavage of linker regions connecting the domains. Proteases causing such cleavage may, for example, be subtilisins, which are known to often exhibit broad substrate specificities [see, e.g.: Grøn et al., *Biochemistry* 31 (1992), pp. 6011–6018; Teplyakov et al., *Protein Engineering* 5 (1992), pp. 413420]. Glycosylation of linker residues in eukaryotes is one Nature's ways of preventing proteolytic degradation. Another is to employ amino acids which are less favoured by the surrounding proteases. The length of the linker also plays a role in relation to accessibility by proteases. Which "solution" is optimal depends on the environment in which the softening protein hybrid is to function. When constructing new CBD hybrid and/or softening protein hybrid molecules, attention will be preferably paid to the linker stability.

Plasmids

Preparation of plasmids capable of expressing fusion proteins having the amino acid sequences derived from fragments of more than one polypeptide is well-known in the art (see, for example, WO 90/00609 and WO 95/16782). The expression cassette may be included within a replication system for episomal maintenance in an appropriate cellular host or may be provided without a replication system, where it may become integrated into the host genome. The DNA may be introduced into the host in accordance with known techniques such as transformation, microinjection or the like.

Once the fused gene has been introduced into the appropriate host, the host may be grown to express the fused gene. Normally it is desirable additionally to add a signal sequence which provides for secretion of the fused gene. Typical examples of useful genes are:

1) Signal sequence—(pro-peptide)—carbohydrate-binding domain—linker—CBD and/or softening protein sequence of interest, or
2) Signal sequence—(pro-peptide)—CBD and/or softening protein sequence of interest—linker—carbohydrate-binding domain, in which the pro-peptide sequence normally contains 5–100, e.g. 5–25, amino acid residues. The recombinant product may be glycosylated or non-glycosylated.

Linking Region

The term "linker" or "linking region" or "Middle region—MR" is intended to indicate a region that might adjoin the CBD and connect it to another CBD or to the amino acid sequence of a softening protein. When present, this linking can be achieved chemically or by recombinant techniques.

An example of the recombinant technique describing the expression of an enzyme with the CBD of different origin is described in S. Karita et al., (1996) Journal of Fermentation and Bioengineering, Vol. 81, No. 6, pp. 553–556. Preferred linking regions are amino acid linking regions (peptides), some examples thereof are described in N. R. Gilkes et al., Microbiol. Rev. 55, 1991, pp. 303–315. The linking region can comprise from 1 to about 100 amino acid residues, in particular of from 2 to 40 amino acid residues, e.g. from 2 to 15 amino acid residues. As stated above, it is preferred to use amino acids which are less favoured by the surrounding proteases. Suitable amino acid linking regions are the *Humicola insolens* family 45 cellulase linker, the NifA gene of *Klebsiella pneumoniae*-CiP linker, the *E. coli* OmpA gene-CiP linker, the E3 cellulase *Thermomonospora fusca* linker and the CenA cellulase linker; preferably the *Humicola insolens* family 45 cellulase linker and the E3 cellulase *Thermomonospora fusca* linker.

Non amino acid/proteinic compounds, referred to as "non-amino acid" can also be used for the linking of the catalytically active amino acid sequence to the CBD:

1) Suitable non-amino acid linking regions are the polyethylene glycol derivatives described in the Shearwater polymers, Inc. catalog of January 1996, such as the nucleophilic PEGs, the carboxyl PEGs, the electrophilically activated PEGs, the sulfhydryl-selective PEGs, the heterofunctional PEGs, the biotin PEGs, the vinyl derivatives, the PEG silanes and the PEG phospholipids. In particular, suitable non-amino acid linking regions are the heterofunctional PEG, (X-PEG-Y) polymers from Shearwater such as PEG(NPC)2, PEG-(NH2)2, t-BOC-NH-PEG-NH2, t-BOC-NH-PEG-CO2NHS, OH-PEG-N H-tBOC, FMOC-NH-PEG-CO2NHS or $PEG(NPC)_2$ MW 3400 from Sigma, glutaric dialdehyde 50 wt % solution in water from Aldrich, disuccinimidyl suberate (DSS) form Sigma, γ-maleimidobutric acid N-hydroxysuccinimide ester (GMBS) from Sigma, 1-ethyl-3-(3-dimethylaminopropyl)carbodiimide hydrochloride (EDC) from Sigma and dimethyl suberimidate hydrochloride (DMS) from Sigma.
2) Other suitable non-amino acid linking regions are 1-ethyl-3-(3-dimethylaminopropyl) carbodiimide, N-ethyl-5-phenylisoaxolium-3-sulphonate, 1-cyclohexyl-3 (2morpholinoethyl) carbodide metho-p-toluene sulphonate, N-ethoxycarbonyl-2-ethoxy 1,2, dihydroquinoline or glutaraldehyde.
3) Also suitable are the crosslinkers described in the 1999/2000 Pierce Products Catalogue from the Pierce Company, under the heading "Cross linking reagents the SMPH, SMCC, LC-SMCC compounds, and preferably the Sulfo-KMUS compound.

Preferred chemical linking regions are PEG(NPC)2, (NH2)2-PEG, t-BOC-NH-PEG-NH2, MAL-PEG-NHS, VS-PEG-NHS polymers from Shearwater and/or the Sulfo-KMUS compound from Pierce.

Fabric Care and Detergent Components

Preferably, the fabric care compositions of the invention will contain at least one additional. fabric care component. The precise nature of these additional components, and levels of incorporation thereof will depend on the physical form of the composition, and the nature of the cleaning operation for which it is to be used.

The composition may comprise optional ingredients such as a dye fixing agent, a fabric softener compound and further optional ingredients. The fabric care compositions of the present invention preferably further comprise a fabric care ingredient selected from cationic surfactants, a transferase enzyme and/or clays.

The composition of the invention can be employed in stand alone product including pre-or post-wash additives. It can also be employed It can also be used in fully-formulated compositions including laundry compositions as well as rinse added fabric softener compositions and dryer added compositions (e.g. sheets) which provide softening and/or antistatic benefits, and rinse added compositions.

Cationic Softeners

The fabric care compositions of the present invention preferably further comprise a cationic surfactant. It has been surprisingly found that the fabric care compositions of the present invention further comprising a cationic surfactant, can provide improved fabric softness and provide, refurbish or restore enhanced tensile strength, anti-wrinkle, anti-bobbling and anti-shrinkage properties to fabrics, as well as provide improved static control, color appearance and fabric anti-wear properties and benefits.

Typical of the cationic softening components are the quaternary ammonium compounds or amine precursors thereof as defined hereinafter.

Quaternary Ammonium Fabric Softening Active Compound (1) Preferred quaternary ammonium fabric softening active compound have the formula

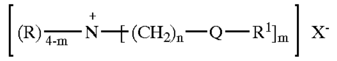
(1)

or the formula:

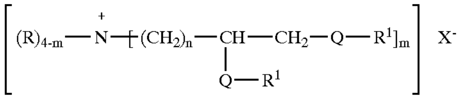
(2)

wherein Q is a functional unit having the formula:

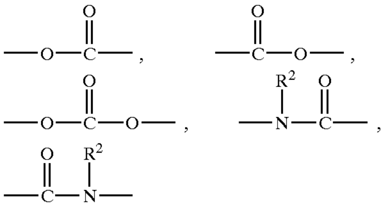

each R unit is independently hydrogen, $C_1$–$C_6$ alkyl, $C_1$–$C_6$ hydroxyalkyl, and mixtures thereof, preferably methyl or hydroxy alkyl; each $R^1$ unit is independently linear or branched $C_{11}$–$C_{22}$ alkyl, linear or branched $C_{11}$–$C_{22}$ alkenyl, and mixtures thereof, $R^2$ is hydrogen, $C_1$–$C_4$ alkyl, $C_1$–$C_4$ hydroxyalkyl, and mixtures thereof; X is an anion which is compatible with fabric softener actives and adjunct ingredients; the index m is from 1 to 4, preferably 2; the index n is from 1 to 4, preferably 2.

An example of a preferred fabric softener active is a mixture of quaternized amines having the formula:

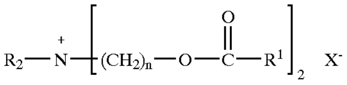

wherein R is preferably methyl; $R^1$ is a linear or branched alkyl or alkenyl chain comprising at least 11 atoms, preferably at least 15 atoms. In the above fabric softener example, the unit —$R^1$ represents a fatty alkyl or alkenyl unit which is typically derived from a triglyceride source. The triglyceride source is preferably derived from tallow, partially hydrogenated tallow, lard, partially hydrogenated lard, vegetable oils and/or partially hydrogenated vegetable oils, such as, canola oil, safflower oil, peanut oil, sunflower oil, corn oil, soybean oil, tall oil, rice bran oil, etc. and mixtures of these oils.

The preferred fabric softening actives of the present invention are the Diester and/or Diamide Quaternary Ammonium (DEQA) compounds, the diesters and diamides having the formula:

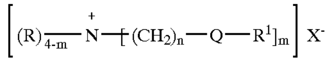

wherein R, $R^1$, X, and n are the same as defined herein above for formulas (1) and (2), and Q has the formula:

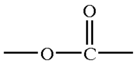
or
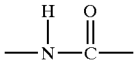

These preferred fabric softening actives are formed from the reaction of an amine with a fatty acyl unit to form an amine intermediate having the formula:

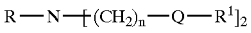

wherein R is preferably methyl, Q and $R^1$ are as defined herein before; followed by quaternization to the final softener active.

Non-limiting examples of preferred amines which are used to form the DEQA fabric softening actives according to the present invention include methyl bis(2-hydroxyethyl) amine having the formula:

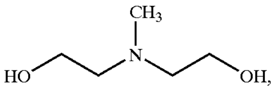

methyl bis(2-hydroxypropyl)amine having the formula:

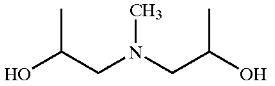

methyl (3-aminopropyl) (2-hydroxyethyl)amine having the formula:

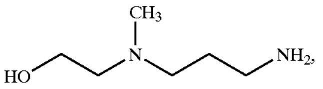

methyl bis(2-aminoethyl)amine having the formula:

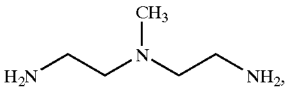

triethanol amine having the formula:

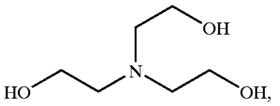

di(2-aminoethyl) ethanolamine having the formula:

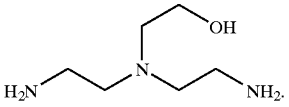

The counterion, $X^{(-)}$ above, can be any softener-compatible anion, preferably the anion of a strong acid, for example, chloride, bromide, methylsulfate, ethylsulfate, sulfate, nitrate and the like, more preferably chloride or methyl sulfate. The anion can also, but less preferably, carry a double charge in which case $X^{(-)}$ represents half a group.

Tallow and canola oil are convenient and inexpensive sources of fatty acyl units which are suitable for use in the present invention as $R^1$ units. The following are non-limiting examples of quaternary ammonium compounds suitable for use in the compositions of the present invention. The term "tallowyl" as used herein below indicates the $R^1$ unit is derived from a tallow triglyceride source and is a mixture of fatty alkyl or alkenyl units. Likewise, the use of the term canolyl refers to a mixture of fatty alkyl or alkenyl units derived from canola oil.

In the following table are described non-limiting examples of suitable fabric softener according to the above formula. In this list, the term "oxy" defines a

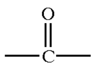

unit, whereas the term "oxo" defines a -O- unit.

Table II

Fabric Softener Actives

N,N-di(tallowyl-oxy-2-oxo-ethyl)-N-methyl, N-(2-hydroxyethyl) ammonium chloride;

N,N-di(canolyl-oxy-2-oxo-ethyl)-N-methyl, N-(2-hydroxyethyl) ammonium chloride;

N,N-di(tallowyloxy-2-oxo-ethyl)-N,N-dimethyl ammonium chloride;

N,N-di(canolyloxy-2-oxo-ethyl)-N,N-dimethyl ammonium chloride

N,N,N-tri(tallowyl-oxy-2-oxo-ethyl)-N-methyl ammonium chloride;

N,N,N-tri(canolyl-oxy-2-oxo-ethyl)-N-methyl ammonium chloride;

N-(tallowyloxy-2-oxo-ethyl)-N-(tallowyl)-N,N-dimethyl ammonium chloride;

N-(canolyloxy-2-oxo-ethyl)-N-(canolyl)-N,N-dimethyl ammonium chloride;

1,2-di(tallowyloxy-oxo)-3-N,N,N-trimethylammoniopropane chloride; and 1,2-di(canolyloxy-oxo)-3-N,N,N-trimethylammoniopropane chloride;

and mixtures of the above actives.

Other examples of quaternay ammoniun softening compounds are methylbis(tallowamidoethyl)(2-hydroxyethyl) ammonium methylsulfate and methylbis(hydrogenated tallowamidoethyl)(2-hydroxyethyl)ammonium methylsulfate; these materials are available from Witco Chemical Company under the trade names Varisoft® 222 and Varisoft® 110, respectively.

Particularly preferred is N,N-di(tallowyl-oxy-2-oxo-ethyl)-N-methyl, N-(2-hydroxyethyl) ammonium chloride, where the tallow chains are at least partially unsaturated.

Transferase Enzyme

The fabric care compositions of the present invention preferably further comprise a transferase enzyme. It has been surprisingly found that the fabric care compositions of the present invention further comprising a transferase enzyme, can provide improved fabric softness and provide, refurbish or restore enhanced tensile strength, anti-wrinkle, anti-bobbling and anti-shrinkage properties to fabrics, as well as provide improved static control, color appearance and fabric anti-wear properties and benefits Transferase enzymes catalyse the transfer of functional compounds to a range of substrates. Particularly, the transferase of the invention have the potential to transfer a chemical moiety, for example a methyl group or a glycosyl group, from a small substrate to form oligomeric molecules or elongate polymeric compounds. Using small substrates, the enzyme improves the properties of garments by binding functional groups like methyl, hydroxymethyl, formyl, carboxyl, aldehyde, ketone, acyl, amino and phosphorous functional groups and/or transferring glycosyl residues to the garment surface.

Without wishing to be bound by theory, it is believed that aminoacyl transferase of the IUPAC Classification EC 2.3.2 links the amino acid(s) of the CBDs, Cross-linked CBDs, the amino acid linking regions and/or the softening proteins to the cotton fibres of the fabric and thereby provide, refurbish or restore tensile strength. Moreover, it is believed that glycosyl transferase of the IUPAC Classification EC 2.4 transfer and link covalently the glycosyl carbohydrates that can be found on the CBDs, Cross-linked CBDs, the amino acid linking regions and/or the softening proteins to the fabric and thereby provide, refurbish or restore tensile strength.

The aminoacyl transferases (EC 2.3.2) are enzymes transferring amino groups from a donor, generally an amino acid, to an acceptor. Even more preferred is the protein-glutamine γ-glutamyltransferase (EC 2.3.2.13), also available under the name transglutaminase.

The general properties of the glycosyltransferases is to transfer a sugar from oligosaccharides to another carbohydrate as acceptor. Both hexosyltransferases and pentosyltransferases can be used in the invention.

Examples of suitable glycosyltransferases are galactosyl transferases and fructosyltransferases, such as 1,4-β-galactosyltransferase; 1,3-α-fructosyltransferase; 2,3-sialyl transferase; cyclodextrin glycosyltransferase; N-acetylgluco- or -galactosaminyltransferase. Of particular interest is EC 2.4.1.24 1,4-α-D-glucan : 1,4-a-D-glucan(D-glucose) 6-α-D-glucosyl transferase. A particulate member of this enzyme is commercially available under the name Transglucosidase L-500.

In addition to the glycosyltransferases discussed above, it has been found that mutant glycosyltransferases and/or glycosidase, examples of which are described in PCT Application Publication No. WO 97/21822 to S. G. Withers Protein Eng. Net. Canada, improve the tensile strength and appearance of fabrics, e.g., reduce fabric wrinkles, enhance shape retention and reduce shrinkage Yet another enzyme that is of particular interest is cyclomaltodextrin glucanotransferase ("CGT-ase") (EC 2.4.1.19), which is commercially available from Amano and Novo Nordisk A/S.

Yet still another group of enzymes that is of particular interest is glucansucrases, of which dextransucrase (EC 2.4.1.5), a glycosyltransferase, is one example. Other glucansucrases that are suitable for use in the compositions described herein include, but are not limited to, various dextransucrases, alternansucrase and levansucrase. Levansucrase is commercially available from Genencor.

These transferases are preferably incorporated into the fabric care compositions in accordance with the invention at a level of from 0.0001% to 10%, more preferably from 0.0005% to 5%, most preferred from 0.001% to 1% pure enzyme by weight of the total composition.

The above-mentioned enzymes may be of any suitable origin, such as vegetable, animal, bacterial, fungal and yeast origin. Origin can further be mesophilic or extremophilic (psychrophilic, psychrotrophic, thermophilic, barophilic, alkalophilic, acidophilic, halophilic, etc.). Purified or non-purified forms of these enzymes may be used. Nowadays, it is common practice to modify wild-type enzymes via protein/genetic engineering techniques in order to optimise their performance efficiency in the fabric care compositions of the invention. For example, the variants may be designed such that the compatibility of the enzyme to commonly encountered ingredients of such compositions is increased. Alternatively, the variant may be designed such that the optimal pH, bleach and/or chelant stability, catalytic activity and the like, of the enzyme variant is tailored to suit the particular fabric conditioning and/or cleaning application.

In particular, attention should be focused on amino acids sensitive to oxidation in the case of bleach stability and on surface charges for the surfactant compatibility. The isoelectric point of such enzymes may be modified by the substitution of some charged amino acids, e.g. an increase in isoelectric point may help to improve compatibility with anionic surfactants. The stability of the enzymes may be further enhanced by the creation of e.g. additional salt bridges and enforcing calcium binding sites to increase chelant stability.

Color Care and Fabric Care Benefits

Technologies which provide a type of color care benefit can also be included. Examples of these technologies are metallo catalysts for color maintenance. Such metallo catalysts are described in copending European Patent Application No. 92870181.2. Dye fixing agents, polyolefin dispersion for anti-wrinkles and improved water absorbancy, perfume and amino-functional polymer (PCT/US97/16546) for colour care treatment and perfume substantivity are further examples of color care/fabric care technologies and are described in the co-pending Patent Application No. 96870140.9, filed Nov. 7, 1996.

Fabric softening agents can also be incorporated into fabric care compositions in accordance with the present invention. These agents may be inorganic or organic in type. Inorganic softening agents are exemplified by the smectite clays disclosed in GB-A-1 400 898 and in U.S. Pat. No. 5,019,292. Organic fabric softening agents include the water insoluble tertiary amines as disclosed in GB-A1 514 276 and EP-B0 011 340 and their combination with mono C1214 C14 quaternary ammonium salts are disclosed in EP-B-0 026 527 and EP-B-0 026 528 and di-long-chain amides as disclosed in EP-B-0 242 919. Other useful organic ingredients of fabric softening systems include high molecular weight polyethylene oxide materials as disclosed in EP-A-0 299 575 and 0 313 146.

Preferably, the fabric care compositions of the present invention will comprise a clay. It has been surprisingly found that the fabric care compositions of the present invention further comprising a clay, can provide improved fabric softness and provide, refurbish or restore enhanced tensile strength, anti-wrinkle, anti-bobbling and anti-shrinkage properties to fabrics, as well as provide improved static control, color appearance and fabric anti-wear properties and benefits.

Levels of smectite clay are normally in the range from 2% to 20%, more preferably from 5% to 15% by weight. Organic fabric softening agents such as the water-insoluble tertiary amines or dilong chain amide materials are incorporated at levels of from 0.5% to 5% by weight, normally from 1% to 3% by weight whilst the high molecular weight polyethylene oxide materials and the water soluble cationic materials are added at levels of from 0.1% to 2%, normally from 0.15% to 1.5% by weight.

Dye Fixing Agent

The composition of the invention may optionally comprise a dye fixing agent. Dye fixing agents, or "fixatives", are well-known, commercially available materials which are designed to improve the appearance of dyed fabrics by minimizing the loss of dye from fabrics due to washing. Not included within this definition are components which are fabric softeners or those described hereinbefore as amino-functional polymers.

Many dye fixing agents are cationic, and are based on various quaternized or otherwise cationically charged organic nitrogen compounds. Cationic fixatives are available under various trade names from several suppliers. Representative examples include: CROSCOLOR PMF (July 1981, Code No. 7894) and CROSCOLOR NOFF (January 1988, Code No. 8544) from Crosfield; INDOSOL E-50 (Feb. 27, 1984, Ref. No. 6008.35.84; polyethyleneamine-based) from Sandoz; SANDOFIX TPS, which is also available from Sandoz and is a preferred polycationic fixative for use herein and SANDOFIX SWE (cationic resinous compound), REWIN SRF, REWIN SRF-O and REWIN DWR from CHT-Beitlich GMBH, Tinofix® ECO, Tinofix® FRD and Solfin® available from Ciba-Geigy.

Other cationic dye fixing agents are described in "Aftertreatments for improving the fastness of dyes on textile fibres" by Christopher C. Cook (REV. PROG. COLORATION Vol. 12, 1982). Dye fixing agents suitable for use in the present invention are ammonium compounds such as fatty acid—diamine condensates e.g. the hydrochloride, acetate, metosulphate and benzyl hydrochloride of oleyldiethyl aminoethylamide, oleylmethyl-diethylenediaminemethosulphate, monostearyl-ethylene diaminotrimethyl-ammonium methosulphate and oxidized products of tertiary amines; derivatives of polymeric alkyldiamines, polyamine-cyanuric chloride condensates and aminated glycerol dichlorohydrins.

A typical amount of the dye fixing agent to be employed in the composition of the invention is preferably up 90% by weight, preferably up to 50% by weight, more preferably from 0.001% to 10% by weight, most preferably from 0.5% to 5% active by weight of the composition.

Fabric Softening Compound

Typical levels of incorporation of the softening compound in the fabric care composition are of from 1% to 80% by weight, preferably from 5% to 75%, more preferably from 15% to 70%, and even more preferably from 19% to 65%, by weight of the composition.

The fabric softener compound is preferably selected from a cationic, nonionic, amphoteric or anionic fabric softening component. Typical of the cationic softening components are the quaternary ammonium compounds or amine precursors thereof as defined hereinafter.

Quaternary Ammonium Fabric Softening Active Compound

As described above, the fabric care compositions of the present invention preferably further comprise a cationic surfacants.

Amine Fabric Softening Active Compound

Suitable amine fabric softening compounds for use herein, which may be in amine form or cationic form are selected from:

(i)- Reaction products of higher fatty acids with a polyamine selected from the group consisting of hydroxyalkylalkylenediamines and dialkylenetriamines and mixtures thereof. These reaction products are mixtures of several compounds in view of the multi-functional structure of the polyamines.

The preferred Component (i) is a nitrogenous compound selected from the group consisting of the reaction product mixtures or some selected components of the mixtures.

One preferred component (i) is a compound selected from the group consisting of substituted imidazoline compounds having the formula:

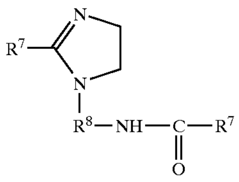

wherein $R^7$ is an acyclic aliphatic $C_{15}$–$C_{21}$ hydrocarbon group and $R^8$ is a divalent $C_1$–$C_3$ alkylene group.

Component (i) materials are commercially available as: Mazamide® 6, sold by Mazer Chemicals, or Ceranine® HC, sold by Sandoz Colors & Chemicals; stearic hydroxyethyl imidazoline sold under the trade names of Alkazine® ST by Alkaril Chemicals, Inc., or Schercozoline® S by Scher Chemicals, Inc.; N,N"-ditallowalkoyldiethylenetriamine; 1-tallowamidoethyl-2-tallowimidazoline (wherein in the preceding structure $R^1$ is an aliphatic $C_{15}$–$C_{17}$ hydrocarbon group and $R^8$ is a divalent ethylene group).

Certain of the Components (i) can also be first dispersed in a Bronsted acid dispersing aid having a pKa value of not greater than about 4; provided that the pH of the final composition is not greater than about 6. Some preferred dispersing aids are hydrochloric acid, phosphoric acid, or methylsulfonic acid.

Both N,N"-ditallowalkoyldiethylenetriamine and 1-tallow(amidoethyl)-2-tallowimidazoline are reaction products of tallow fatty acids and diethylenetriamine, and are precursors of the cationic fabric softening agent methyl-1-tallowamidoethyl-2-tallowimidazolinium methylsulfate (see "Cationic Surface Active Agents as Fabric Softeners," R. R. Egan, Journal of the American Oil Chemicals'Society, January 1978, pages 118–121). N,N"-ditallow alkoyldiethylenetriamine and 1-tallowamidoethyl-2-tallowimidazoline can be obtained from Witco Chemical Company as experimental chemicals. Methyl-1-tallowamidoethyl-2-tallowimidazolinium methylsulfate is sold by Witco Chemical Company under the tradename Varisoft® 475.

(ii)-softener having the formula:

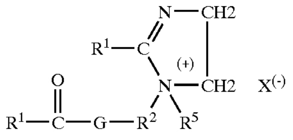

wherein each $R^2$ is a $C_{1-6}$ alkylene group, preferably an ethylene group; and G is an oxygen atom or an —NR— group; and each R, $R^1$, $R^2$ and $R^5$ have the definitions given above and $A^-$ has the definitions given above for $X^-$.

An example of Compound (ii) is 1-oleylamidoethyl-2-oleylimidazolinium chloride wherein $R^1$ is an acyclic aliphatic $C_{15}$–$C_{17}$ hydrocarbon group, $R^2$ is an ethylene group, G is a NH group, $R^5$ is a methyl group and $A^-$ is a chloride anion.

(iii)-softener having the formula:

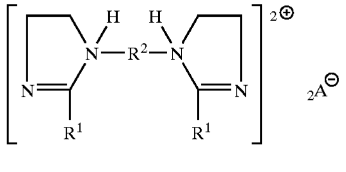

wherein R, $R^1$, $R^2$, and $A^-$ are defined as above.

An example of Compound (iii) is the compound having the formula:

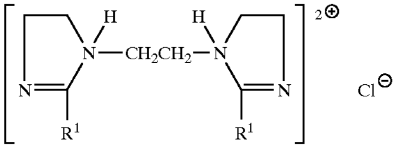

wherein $R^1$ is derived from oleic acid.

Additional fabric softening agents useful herein are described in U.S. Pat. No. 4,661,269, issued Apr. 28, 1987, in the names of Toan Trinh, Errol H. Wahl, Donald M. Swartley, and Ronald L. Hemingway; U.S. Pat. No. 4,439,335, Burns, issued Mar. 27, 1984; and in U.S. Pat. No. 3,861,870, Edwards and Diehl; U.S. Pat. No. 4,308,151, Cambre; U.S. Pat. No. 3,886,075, Bernardino; U.S. Pat. No. 4,233,164, Davis; U.S. Pat. No. 4,401,578, Verbruggen; U.S. Pat. No. 3,974,076, Wiersema and Rieke; U.S. Pat. No. 4,237,016, Rudkin, Clint, and Young; and European Patent Application publication No. 472,178, by Yamamura et al., all of said documents being incorporated herein by reference.

Of course, the term "softening active" can also encompass mixed softening active agents. Preferred among the classes of softener compounds disclosed herein before are the diester or diamido quaternary ammonium fabric softening active compound (DEQA).

Fully formulated fabric care compositions may contain, in addition to the hereinbefore described components, one or more of the following. ingredients.

Liquid Carrier

Another optional, but preferred, ingredient is a liquid carrier. The liquid carrier employed in the instant compositions is preferably at least primarily water due to its low cost, relative availability, safety, and environmental compatibility. The level of water in the liquid carrier is preferably at least about 50%, most preferably at least about 60%, by weight of the carrier. Mixtures of water and low molecular weight, e.g., <about 200, organic solvent, e.g., lower alcohols such as ethanol, propanol, isopropanol or butanol are useful as the carrier liquid. Low molecular weight alcohols include monohydric, dihydric (glycol, etc.) trihydric (glycerol, etc.), and higher polyhydric (polyols) alcohols.

Additional Solvents

The compositions of the present invention may comprise one or more solvents which provide increased ease of formulation. These ease of formulation solvents are all disclosed in WO 97/03169. This is particularly the case when formulating liquid, clear fabric softening compositions. When employed, the ease of formulation solvent system preferably comprises less than about 40%, preferably from about 10% to about 35%, more preferably from about 12% to about 25%, and even more preferably from about 14% to about 20%, by weight of the composition. The ease of formulation solvent is selected to minimize solvent odor impact in the composition and to provide a low viscosity to the final composition. For example, isopropyl alcohol is not very effective and has a strong odor. n-Propyl alcohol is more effective, but also has a distinct odor. Several butyl alcohols also have odors but can be used for effective clarity/stability, especially when used as part of a ease of formulation solvent system to minimize their odor. The alcohols are also selected for optimum low temperature stability, that is they are able to form compositions that are liquid with acceptable low viscosities and translucent, preferably clear, down to about 40° F. (about 4.4° C.) and are able to recover after storage down to about 20° F. (about minus 6.7° C.).

The suitability of any ease of formulation solvent for the formulation of the liquid, concentrated, preferably clear, fabric softener compositions herein with the requisite stability is surprisingly selective. Suitable solvents can be selected based upon their octanol/water partition coefficient (P) as defined in WO 97/03169.

The ease of formulation solvents herein are selected from those having a ClogP of from about 0.15 to about 0.64, preferably from about 0.25 to about 0.62, and more preferably from about 0.40 to about 0.60, said ease of formulation solvent preferably being at least somewhat asymmetric, and preferably having a melting, or solidification, point that allows it to be liquid at, or near room temperature. Solvents that have a low molecular weight and are biodegradable are also desirable for some purposes. The more assymetric solvents appear to be very desirable, whereas the highly symmetrical solvents such as 1,7-heptanediol, or 1,4-bis (hydroxymethyl) cyclohexane, which have a center of symmetry, appear to be unable to provide the essential clear compositions when used alone, even though their ClogP values fall in the preferred range. The most preferred ease of formulation solvents can be identified by the appearance of the softener vesicles, as observed via cryogenic electron microscopy of the compositions that have been diluted to the concentration used in the rinse. These dilute compositions appear to have dispersions of fabric softener that exhibit a more unilamellar appearance than conventional fabric softener compositions. The closer to uni-lamellar the appearance, the better the compositions seem to perform. These compositions provide surprisingly good fabric softening as compared to similar compositions prepared in the conventional way with the same fabric softener active.

Operable ease of formulation solvents are disclosed and listed below which have ClogP values which fall within the requisite range. These include monools, C6 diols, C7 diols, octanediol isomers, butanediol derivatives, trinethylpentanediol isomers, ethyl methylpentanediol isomers, propyl pentanediol isomers, dimethylhexanediol isomers, ethylhexanediol isomers, methylheptanediol isomers, octanediol isomers, nonanediol isomers, alkyl glyceryl ethers, di(hydroxy alkyl) ethers, and aryl glyceryl ethers, aromatic glyceryl ethers, alicyclic diols and derivatives, $C_3C_7$ diol alkoxylated derivatives, aromatic diols, and unsaturated diols. Particularly preferred ease of formulation solvents include hexanediols such as 1,2-Hexanediol and 2-Ethyl-1,3-hexanediol and pentanediols such as 2,2,4-Trimethyl-1,3-pentanediol.

Dispersibility Aids

Relatively concentrated compositions containing both saturated and unsaturated diester quaternary ammonium compounds can be prepared that are stable without the addition of concentration aids. However, the compositions of the present invention may require organic and/or inorganic concentration aids to go to even higher concentrations and/or to meet higher stability standards depending on the other ingredients. These concentration aids which typically can be viscosity modifiers may be needed, or preferred, for ensuring stability under extreme conditions when particular softener active levels are used. The surfactant concentration aids are typically selected from the group consisting of (1) single long chain alkyl cationic surfactants; (2) nonionic surfactants; (3) amine oxides; (4) fatty acids; and (5) mixtures thereof. These aids are described in WO 94/20597, specifically on page 14, line 12 to page 20, line 12, which is herein incorporated by reference.

When said dispersibility aids are present, the total level is from 2% to 25%, preferably from 3% to 17%, more preferably from 4% to 15%, and even more preferably from 5% to 13% by weight of the composition. These materials can either be added as part of the active softener raw material, (I), e.g., the monolong chain alkyl cationic surfactant and/or the fatty acid which are reactants used to form the biodegradable fabric softener active as discussed hereinbefore, or added as a separate component. The total level of dispersibility aid includes any amount that may be present as part of component (1).

Inorganic viscosity/dispersibility control agents which can also act like or augment the effect of the surfactant concentration aids, include water-soluble, ionizable salts which can also optionally be incorporated into the compositions of the present invention. A wide variety of ionizable salts can be used. Examples of suitable salts are the halides of the Group IA and IIA metals of the Periodic Table of the Elements, e.g., calcium chloride, magnesium chloride, sodium chloride, potassium bromide, and lithium chloride. The ionizable salts are particularly useful during the process of mixing the ingredients to make the compositions herein, and later to obtain the desired viscosity. The amount of ionizable salts used depends on the amount of active ingredients used in the compositions and can be adjusted according to the desires of the formulator. Typical levels of salts used to control the composition viscosity are from about 20 to about 20,000 parts per million (ppm), preferably from about 20 to about 11,000 ppm, by weight of the composition.

Alkylene polyammonium salts can be incorporated into the composition to give viscosity control in addition to or in place of the water-soluble, ionizable salts above. In addition, these agents can act as scavengers, forming ion pairs with anionic detergent carried over from the main wash, in the rinse, and on the fabrics, and may improve softness performance. These agents may stabilize the viscosity over a broader range of temperature, especially at low temperatures, compared to the inorganic electrolytes.

Specific examples of alkylene polyammonium salts include I-lysine monohydrochloride and 1,5-diammonium 2-methyl pentane dihydrochloride.

Stabilizers

Stabilizers can be present in the compositions of the present invention. The term "stabilizer," as used herein, includes antioxidants and reductive agents. These agents are present at a level of from 0% to about 2%, preferably from about 0.01% to about 0.2%, more preferably from about 0.035% to about 0.1% for antioxidants, and more preferably from about 0.01% to about 0.2% for reductive agents. These assure good odor stability under long term storage conditions for the compositions and compounds stored in molten form. The use of antioxidants and reductive agent stabilizers is especially critical for low scent products (low perfume).

Examples of antioxidants that can be added to the compositions of this invention include a mixture of ascorbic acid, ascorbic palmitate, propyl gallate, available from Eastman Chemical Products, Inc., under the trade names Tenox® PG and Tenox S-1; a mixture of BHT (butylated hydroxytoluene), BHA (butylated hydroxyanisole), propyl gallate, and citric acid, available from Eastman Chemical Products, Inc., under the trade name Tenox-6; butylated hydroxytoluene, available from UOP Process Division under the trade name Sustane® BHT; tertiary butylhydroquinone, Eastman Chemical Products, Inc., as Tenox TBHQ; natural tocopherols, Eastman Chemical Products, Inc., as Tenox GT-1IGT-2; and butylated hydroxyanisole, Eastman Chemical Products, Inc., as BHA;

long chain esters ($C_8$–$C_{22}$) of gallic acid, e.g., dodecyl gallate; Irganox® 1010; Irganox® 1035; Irganox® B 1171; Irganox® 1425; Irganox® 3114; Irganox® 3125; and mixtures thereof; preferably Irganox® 3125, Irganox® 1425, Irganox ® 3114, and mixtures thereof; more preferably Irganoxe 3125 alone. The chemical names and CAS numbers for some of the above stabilizers are listed in Table II below.

TABLE II

| Antioxidant | CAS No. | Chemical Name used in Code of Federal Regulations |
|---|---|---|
| Irganox ® 1010 | 6683-19-8 | Tetrakis(methylene(3,5-di-tert-butyl-4-hydroxyhydrocinnamate))methane |
| Irganox ® 1035 | 41484-35-9 | Thiodiethylene bis(3,5-di-tert-butyl-4-hydroxyhydrocinnamate) |
| Irganox ® 1098 | 23128-74-7 | N,N'-Hexamethylene bis(3,5-di-tert-butyl-4-hydroxyhydrocinnamamide) |
| Irganox ® B 1171 | 31570-04-4 | |
| | 23128-74-7 | 1:1 Blend of Irganox ® 1098 and Irgafos ® 168 |
| Irganox ® 1425 | 65140-91-2 | Calcium bis(monoethyl(3,5-di-tert-butyl-4-hydroxybenzyl)phosphonate) |
| Irganox ® 3114 | 65140-91-2 | Calcium bis(monoethyl(3,5-di-tert-butyl-4-hydroxybenzyl)phosphonate) |
| Irganox ® 3125 | 34137-09-2 | 3,5-Di-tert-butyl-4-hydroxy-hydrocinnamic acid triester with 1,3,5-tris(2-hydroxyethyl)-S-triazine-2,4,6-(1H, 3H, 5H)-trione |
| Irgafos ® 168 | 31570-04-4 | Tris(2,4-di-tert-butyl-phenyl)-phosphite |

Examples of reductive agents include sodium borohydride, hypophosphorous acid, Irgafos® 168, and mixtures thereof.

Soil Release Agent

Soil Release agents are desirably used in fabric care compositions of the instant invention. Any polymeric soil release agent known to those skilled in the art can optionally be employed in the compositions of this invention. Polymeric soil release agents are characterized by having both hydrophilic segments, to hydrophilize the surface of hydrophobic fibers, such as polyester and nylon, and hydrophobic segments, to deposit upon hydrophobic fibers and remain adhered thereto through completion of washing and rinsing cycles and, thus, serve as an anchor for the hydrophilic segments. This can enable stains occurring subsequent to treatment with the soil release agent to be more easily cleaned in later washing procedures.

If utilized, soil release agents will generally comprise from about 0.01% to about 10.0%, by weight, of the fabric care compositions herein, typically from about 0.1% to about 5%, preferably from about 0.2% to about 3.0%.

The following, all included herein by reference, describe soil release polymers suitable for use in the present invention. U.S. Pat. No. 3,959,230 Hays, issued May 25, 1976; U.S. Pat. No. 3,893,929 Basadur, issued Jul. 8, 1975; U.S. Pat. No. 4,000,093, Nicol, et al., issued Dec. 28, 1976; U.S. Pat. No. 4,702,857 Gosselink, issued Oct. 27, 1987; U.S. Pat. No. 4,968,451, Scheibel et al., issued November 6; U.S. Pat. No. 4,702,857, Gosselink, issued Oct. 27, 1987; U.S. Pat. No. 4,711,730, Gosselink et al., issued Dec. 8, 1987, U.S. Pat. No. 4,721,580, Gosselink, issued Jan. 26, 1988; U.S. Pat. No. 4,877,896, Maldonado et al., issued Oct. 31, 1989; U.S. Pat. No. 4,956,447, Gosselink et al., issued Sep. 11, 1990; U.S. Pat. No. 5,415,807 Gosselink et al., issued May 16, 1995; European Patent Application 0 219 048, published Apr. 22, 1987 by Kud, et al.

Further suitable soil release agents are described in U.S. Pat. No. 4,201,824, Violland et al.; U.S. Pat. No. 4,240,918 Lagasse et al.; U.S. Pat. No. 4,525,524 Tung et al.; U.S. Pat. No. 4,579,681, Ruppert et al.; U.S. Pat. Nos. 4,240,918; 4,787,989; 4,525,524; EP 279,134 A, 1988, to Rhone-Poulenc Chemie; EP 457,205 A to BASF (1991); and DE 2,335,044 to Unilever N. V., 1974 all incorporated herein by reference.

Commercially available soil release agents include the METOLOSE SM100, METOLOSE SM200 manufactured by Shin-etsu Kagaku Kogyo K.K., SOKALAN type of material, e.g., SOKALAN HP-22, available from BASF (Germany), ZELCON 5126 (from Dupont) and MILEASE T (from ICI).

Bactericides

Examples of bactericides used in the compositions of this invention include glutaraldehyde, formaldehyde, 2-bromo-2-nitro-propane-1,3-diol sold by Inolex Chemicals, located in Philadelphia, Pa., under the trade name Bronopol®, and a mixture of 5-chloro-2-methyl4-isothiazoline-3-one and 2-methyl4-isothiazoline-3-one sold by Rohm and Haas Company under the trade name Kathon 1 to 1,000 ppm by weight of the agent.

Perfume

The present invention can contain a perfume. Suitable perfumes are disclosed in U.S. Pat. No. 5,500,138, said patent being incorporated herein by reference. As used herein, perfume includes fragrant substance or mixture of substances including natural (i.e., obtained by extraction of flowers, herbs, leaves, roots, barks, wood, blossoms or plants), artificial (i.e., a mixture of different nature oils or oil constituents) and synthetic (i.e., synthetically produced) odoriferous substances. Such materials are often accompanied by auxiliary materials, such as fixatives, extenders, stabilizers and solvents. These auxiliaries are also included within the meaning of "perfume", as used herein. Typically, perfumes are complex mixtures of a plurality of organic compounds.

The range of the natural raw substances can embrace not only readily-volatile, but also moderately-volatile and slightly-volatile components and that of the synthetics can include representatives from practically all classes of fragrant substances, as will be evident from the following illustrative compilation: natural products, such as tree moss absolute, basil oil, citrus fruit oils (such as bergamot oil, mandarin oil, etc.), mastix absolute, myrtle oil, palmarosa oil, patchouli oil, petitgrain oil Paraguay, wormwood oil, alcohols, such as farnesol, geraniol, linalool, nerol, phenylethyl alcohol, rhodinol, cinnamic alcohol, aldehydes, such as citral, Helional™, alpha-hexyl-cinnamaldehyde, hydroxycitronellal, Lilial™ (p-tert-butyl-alpha-methyldihydrocinnamaldehyde), methyinonylacetaldehyde, ketones, such as allylionone, alpha-ionone, beta-ionone, isoraldein (isomethyl-alpha-ionone), methylionone, esters, such as allyl phenoxyacetate, benzyl salicylate, cinnamyl propionate, citronellyl acetate, citronellyl ethoxolate, decyl acetate, dimethylbenzylcarbinyl acetate, dimethylbenzylcarbinyl butyrate, ethyl acetoacetate, ethyl acetylacetate, hexenyl isobutyrate, linalyl acetate, methyl dihydrojasmonate, styrallyl acetate, vetiveryl acetate, etc., lactones, such as gamma-undecalactone, various components often used in perfumery, such as musk ketone, indole, p-menthane-8-thiol-3-one, and methyl-eugenol. Likewise, any conventional fragrant acetal or ketal known in the art can be added to the present composition as an optional component of the conventionally formulated perfume (c). Such conventional fragrant acetals and ketals include the well-known methyl and ethyl acetals and ketals, as well as acetals or ketals based on benzaldehyde, those comprising phenylethyl moieties, or more recently developed specialties such as those described in a United States Patent entitled "Acetals and Ketals of Oxo-Tetralins and Oxo-Indanes, see U.S. Pat. No. 5,084, 440, issued Jan. 28, 1992, assigned to Givaudan Corp. Of course, other recent synthetic specialties can be included in the perfume compositions for fully-formulated fabric softening compositions. These include the enol ethers of alkyl-substituted oxo-tetralins and oxo-indanes as described in U.S. Pat. 5,332,725, Jul. 26, 1994, assigned to Givaudan; or Schiff Bases as described in U.S. Pat. 5,264,615, Dec. 9, 1991, assigned to Givaudan.

The perfumes useful in the present invention compositions are substantially free of halogenated materials and nitromusks.

Perfume can be present at a level of from 0% to 10%, preferably from 0.1% to 5%, and more preferably from 0.2% to 3%, by weight of the finished composition. Fabric care compositions of the present invention provide improved fabric perfume deposition.

Crystal Growth Inhibitor Component

The fabric care compositions of the present invention can further contain a crystal growth inhibitor component, preferably an organodiphosphonic acid component, incorporated preferably at a level of from 0.01% to 5%, more preferably from 0.1% to 2% by weight of the compositions.

By organo diphosphonic acid it is meant herein an organo diphosphonic acid which does not contain nitrogen as part of its chemical structure. This definition therefore excludes the organo aminophosphonates, which however may be included in compositions of the invention as heavy metal ion sequestrant components.

The organo diphosphonic acid is preferably a $C_1$–$C_4$ diphosphonic acid, more preferably a $C_2$ diphosphonic acid, such as ethylene diphosphonic acid, or most preferably ethane 1-hydroxy-1,1-diphosphonic acid (HEDP) and may be present in partially or fully ionized form, particularly as a salt or complex.

Enzyme

The compositions and processes herein can optionally employ one or more enzymes such as lipases, proteases, cellulase, amylases and peroxidases. A preferred enzyme for use herein is a cellulase enzyme. Indeed, this type of enzyme will further provide a color care benefit to the treated fabric. Cellulases usable herein include both bacterial and fungal types, preferably having a pH optimum between 5 and 9.5. U.S. Pat. No. 4,435,307 discloses suitable fungal cellulases from Humicola insolens or Humicola strain DSM1800 or a cellulase 212-producing fungus belonging to the genus Aeromonas, and cellulase extracted from the hepatopancreas of a marine mollusk, Dolabella Auricula Solander. Suitable cellulases are also disclosed in GB-A-2.075.028; GB-A-2.095.275 and DE-OS-2.247.832. CAREZYME® and CELLUZYME® (Novo) are especially useful. Other suitable cellulases are also disclosed in WO 91/17243 to Novo, WO 96134092, WO 96134945 and EP-A-0,739,982. In practical terms for current commercial preparations, typical amounts are up to 5 mg by weight, more typically 0.0001 mg to 3 mg, of active enzyme per gram of the detergent composition. Stated otherwise, the compositions herein will typically comprise from 0.001% to 5%, preferably 0.01%–1% by weight of a commercial enzyme preparation. In the particular cases where activity of the enzyme preparation can be defined otherwise such as with cellulases, corresponding activity units can also be used (e.g. CEVU or cellulase Equivalent Viscosity Units). For instance, the compositions of the present invention can contain cellulase enzymes at a level equivalent to an activity from 0.5 to 1000 CEVU/gram of composition. Cellulase enzyme preparations used for the purpose of formulating the compositions of this invention typically have an activity comprised between 1,000 and 10,000 CEVU/gram in liquid or solid form.

Other Optional Ingredients

The present invention can include optional components conventionally used in textile treatment compositions, for example: brighteners, colorants; surfactants; anti-shrinkage agents; fabric crisping agents; spotting agents; germicides; fungicides; anti-oxidants such as butylated hydroxy toluene, anti-corrosion agents, antifoam agents, and the like.

The present invention can also include other compatible ingredients, including those as disclosed in WO96/02625, WO96/21714, and WO96/21715, and dispersible polyolefin such as Velustrol® as disclosed in co-pending application PCT/US 97/01644, and the like. The present invention can also contain optional chelating agents.

Applications

The compositions of the invention are suitable for use in any steps of the domestic treatment, that is as a pre-treatment composition, as a wash additive as a composition suitable for use in the rinse-cycle of the laundry cycle or applied on a dryer-sheet. Obviously, for the purpose of the invention, multiple applications can be made such as treating the fabric with a pre-treatment composition of the invention and also thereafter with a composition of the invention suitable for use in the rinse cycle and/or suitable for use as a dryer-sheet. The compositions of the invention may also be in a spray, foam, or aerosol form which for example can be suitable for use while ironing, or applied on the surfaces of the tumble dryer.

Surfactant System

The fabric care compositions when formulated as laundry softening through-the-wash compositions according to the present invention generally comprise a surfactant system wherein the surfactant can be selected from nonionic and/or anionic and/or cationic and/or ampholytic and/or zwitterionic and/or semi-polar surfactants.

The surfactant is typically present at a level of from 0.1% to 60% by weight. More preferred levels of incorporation are 1% to 35% by weight, most preferably from 1% to 30% by weight of fabric care compositions in accord with the invention.

The surfactant is preferably formulated to be compatible with enzyme components present in the composition. In liquid or gel compositions the surfactant is most preferably formulated such that it promotes, or at least does not degrade, the stability of any enzyme in these compositions.

Preferred surfactant systems to be used according to the present invention comprise as a surfactant one or more of the nonionic and/or anionic surfactants described herein.

Polyethylene, polypropylene, and polybutylene oxide condensates of alkyl phenols are suitable for use as the nonionic surfactant of the surfactant systems of the present invention, with the polyethylene oxide condensates being preferred. These compounds include the condensation products of alkyl phenols having an alkyl group containing from about 6 to about 14 carbon atoms, preferably from about 8 to about 14 carbon atoms, in either a straight-chain or branched-chain configuration with the alkylene oxide. In a preferred embodiment, the ethylene oxide is present in an amount equal to from about 2 to about 25 moles, more preferably from about 3 to about 15 moles, of ethylene oxide per mole of alkyl phenol. Commercially available nonionic surfactants of this type include Igepal™ CO-630, marketed by the GAF Corporation; and Triton™ X45, X-114, X-100 and X-102, all marketed by the Rohm & Haas Company.

These surfactants are commonly referred to as alkylphenol alkoxylates (e.g., alkyl phenol ethoxylates).

The condensation products of primary and secondary aliphatic alcohols with from about 1 to about 25 moles of ethylene oxide are suitable for use as the nonionic surfactant of the nonionic surfactant systems of the present invention. The alkyl chain of the aliphatic alcohol can either be straight or branched, primary or secondary, and generally contains from about 8 to about 22 carbon atoms. Preferred are the condensation products of alcohols having an alkyl group containing from about 8 to about 20 carbon atoms, more preferably from about 10 to about 18 carbon atoms, with from about 2 to about 10 moles of ethylene oxide per mole of alcohol. About 2 to about 7 moles of ethylene oxide and most preferably from 2 to 5 moles of ethylene oxide per mole of alcohol are present in said condensation products. Examples of commercially available nonionic surfactants of this type include Tergitol™ 15-S-9 (the condensation product of $C_{1\ 1}$–$C_{15}$ linear alcohol with 9 moles ethylene oxide), Tergitol™ 24-L-6 NMW (the condensation product of $C_{12}$–$C_{14}$ primary alcohol with 6 moles ethylene oxide with a narrow molecular weight distribution), both marketed by Union Carbide Corporation; Neodol™ 45-9 (the condensation product of $C_{14}$–$C_{15}$ linear alcohol with 9 moles of ethylene oxide), Neodol™ 23-3 (the condensation product of $C_{12}$–$C_{13}$ linear alcohol with 3.0 moles of ethylene oxide), Neodol™ 45-7 (the condensation product of $C_{14}$–$C_{15}$ linear alcohol with 7 moles of ethylene oxide), Neodol™ 45-5 (the condensation product of $C_{14}$–$C_{15}$ linear alcohol with 5 moles of ethylene oxide) marketed by Shell Chemical Company, Kyro™ EOB (the condensation product of $C_{13}$–$C_{15}$ alcohol with 9 moles ethylene oxide), marketed by The Procter & Gamble Company, and Genapol LA O3O or O5O (the condensation product of $C_{12}$–$C_{14}$ alcohol with 3 or 5 moles of ethylene oxide) marketed by Hoechst. Preferred range of HLB in these products is from 8–11 and most preferred from 8–10.

Also useful as the nonionic surfactant of the surfactant systems of the present invention are the alkylpolysaccharides disclosed in U.S. Pat. No. 4,565,647, Lienado, issued Jan. 21, 1986, having a hydrophobic group containing from about 6 to about 30 carbon atoms, preferably from about 10 to about 16 carbon atoms and a polysaccharide, e.g. a polyglycoside, hydrophilic group containing from about 1.3 to about 10, preferably from about 1.3 to about 3, most preferably from about 1.3 to about 2.7 saccharide units. Any reducing saccharide containing 5 or 6 carbon atoms can be used, e.g., glucose, galactose and galactosyl moieties can be substituted for the glucosyl moieties (optionally the hydrophobic group is attached at the 2-, 3-, 4-, etc. positions thus giving a glucose or galactose as opposed to a glucoside or galactoside). The intersaccharide bonds can be, e.g., between the one position of the additional saccharide units and the 2-, 3, 4-, and/or 6- positions on the preceding saccharide units. The preferred alkylpolyglycosides have the formula $$R^2O(C_nH_{2n}O)_t(\text{glycosyl})_x$$

wherein $R^2$ is selected from the group consisting of alkyl, alkylphenyl, hydroxyalkyl, hydroxyalkylphenyl, and mixtures thereof in which the alkyl groups contain from about 10 to about 18, preferably from about 12 to about 14, carbon atoms; n is 2 or 3, preferably 2; t is from 0 to about 10, preferably 0; and x is from about 1.3 to about 10, preferably from about 1.3 to about 3, most preferably from about 1.3 to about 2.7. The glycosyl is preferably derived from glucose. To prepare these compounds, the alcohol or alkylpolyethoxy alcohol is formed first and then reacted with glucose, or a source of glucose, to form the glucoside (attachment at the 1-position). The additional glycosyl units can then be attached between their 1-position and the preceding glycosyl units 2-, 3-, 4- and/or 6-position, preferably predominately the 2-position.

The condensation products of ethylene oxide with a hydrophobic base formed by the condensation of propylene oxide with propylene glycol are also suitable for use as the additional nonionic surfactant systems of the present invention. The hydrophobic portion of these compounds will preferably have a molecular weight of from about 1500 to about 1800 and will exhibit water insolubility. The addition of polyoxyethylene moieties to this hydrophobic portion tends to increase the water solubility of the molecule as a whole, and the liquid character of the product is retained up to the point where the polyoxyethylene content is about 50% of the total weight of the condensation product, which corresponds to condensation with up to about 40 moles of ethylene oxide. Examples of compounds of this type include certain of the commercially-available Plurafac™ LF404 and Pluronic™ surfactants, marketed by BASF.

Also suitable for use as the nonionic surfactant of the nonionic surfactant system of the present invention, are the condensation products of ethylene oxide with the product resulting from the reaction of propylene oxide and ethylenediamine. The hydrophobic moiety of these products consists of the reaction product of ethylenediamine and excess propylene oxide, and generally has a molecular weight of from about 2500 to about 3000. This hydrophobic moiety is condensed with ethylene oxide to the extent that the condensation product contains from about 40% to about 80% by weight of polyoxyethylene and has a molecular weight of from about 5,000 to about 11,000. Examples of this type of nonionic surfactant include certain of the commercially available Tetronic™ compounds, marketed by BASF.

Preferred for use as the nonionic surfactant of the surfactant systems of the present invention are polyethylene oxide condensates of alkyl phenols, condensation products of primary and secondary aliphatic alcohols with from about 1 to about 25 moles of ethylene oxide, alkylpolysaccharides, and mixtures thereof. Most preferred are $C_8$–$C_{14}$ alkyl phenol ethoxylates having from 3 to 15 ethoxy groups and $C_8$–$C_{18}$ alcohol ethoxylates (preferably $C_{10}$ avg.) having from 2 to 10 ethoxy groups, and mixtures thereof.

Highly preferred nonionic surfactants are polyhydroxy fatty acid amide surfactants of the formula.

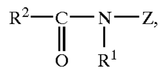

wherein $R^1$ is H, or $R^1$ is $C_{1-4}$ hydrocarbyl, 2-hydroxy ethyl, 2-hydroxy propyl or a mixture thereof, $R^2$ is $C_{5-31}$ hydrocarbyl, and Z is a polyhydroxyhydrocarbyl having a linear hydrocarbyl chain with at least 3 hydroxyls directly connected to the chain, or an alkoxylated derivative thereof. Preferably, $R^1$ is methyl, $R^2$ is a straight $C_{11-15}$ alkyl or $C_{16-18}$ alkyl or alkenyl chain such as coconut alkyl or mixtures thereof, and Z is derived from a reducing sugar such as glucose, fructose, maltose, lactose, in a reductive amination reaction.

Suitable anionic surfactants to be used are linear alkyl benzene sulfonate, alkyl ester sulfonate surfactants including linear esters of $C_8$–$C_{20}$ carboxylic acids (i.e., fatty acids) which are sulfonated with gaseous $SO_3$ according to "The Journal of the American Oil Chemists Society", 52 (1975), pp. 323–329. Suitable starting materials would include natural fatty substances as derived from tallow, palm oil, etc.

The preferred alkyl ester sulfonate surfactant, especially for laundry applications, comprise alkyl ester sulfonate surfactants of the structural formula:

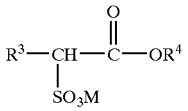

wherein $R^3$ is a $C_8$–$C_{20}$ hydrocarbyl, preferably an alkyl, or combination thereof, $R^4$ is a $C_1$–$C_6$ hydrocarbyl, preferably an alkyl, or combination thereof, and M is a cation which forms a water soluble salt with the alkyl ester sulfonate. Suitable salt-forming cations include metals such as sodium, potassium, and lithium, and substituted or unsubstituted ammonium cations, such as monoethanolamine, diethanolamine, and triethanolamine. Preferably, $R^3$ is $C_{10}$–$C_{16}$ alkyl, and $R^4$ is methyl, ethyl or isopropyl. Especially preferred are the methyl ester sulfonates wherein $R^3$ is $C_{10}$–$C_{16}$ alkyl.

Other suitable anionic surfactants include the alkyl sulfate surfactants which are water soluble salts or acids of the formula $ROSO_3M$ wherein R preferably is a $C_{10}$–$C_{24}$ hydrocarbyl, preferably an alkyl or hydroxyalkyl having a $C_{10}$–$C_{20}$ alkyl component, more preferably a $C_{12}$–$C_{18}$ alkyl or hydroxyalkyl, and M is H or a cation, e.g., an alkali metal cation (e.g. sodium, potassium, lithium), or ammonium or substituted ammonium (e.g. methyl-, dimethyl-, and trimethyl ammonium cations and quaternary ammonium cations such as tetramethyl-ammonium and dimethyl piperdinium cations and quaternary ammonium cations derived from alkylamines such as ethylamine, diethylamine, triethylamine, and mixtures thereof, and the like). Typically, alkyl chains of $C_{12}$–$C_{16}$ are preferred for lower wash temperatures (e.g. below about 50° C.) and $C_{16-18}$ alkyl chains are preferred for higher wash temperatures (e.g. above about 50° C.).

Other anionic surfactants useful for detersive purposes can also be included in the fabric care compositions of the present invention. These can include salts (including, for example, sodium, potassium, ammonium, and substituted ammonium salts such as mono-, di- and triethanolamine salts) of soap, $C_8$–$C_{22}$ primary of secondary alkanesulfonates, $C_8$–$C_{24}$ olefinsulfonates, sulfonated polycarboxylic acids prepared by sulfonation of the pyrolyzed product of alkaline earth metal citrates, e.g., as described in British patent specification No. 1,082,179, $C_8$–$C_{24}$ alkylpolyglycolethersulfates (containing up to 10 moles of ethylene oxide); alkyl glycerol sulfonates, fatty acyl glycerol sulfonates, fatty oleyl glycerol sulfates, alkyl phenol ethylene oxide ether sulfates, paraffin sulfonates, alkyl phosphates, isethionates such as the acyl isethionates, N-acyl taurates, alkyl succinamates and sulfosuccinates, monoesters of sulfosuccinates (especially saturated and unsaturated $C_{12}$–$C_{18}$ monoesters) and diesters of sulfosuccinates (especially saturated and unsaturated $C_6$–$C_{12}$ diesters), acyl sarcosinates, sulfates of alkylpolysaccharides such as the sulfates of alkylpolyglucoside (the nonionic nonsulfated compounds being described below), branched primary alkyl sulfates, and alkyl polyethoxy carboxylates such as those of the formula $RO(CH_2CH_2O)_k$—$CH_2COO$—M+ wherein R is a $C_8$–$C_{22}$ alkyl, k is an integer from 1 to 10, and M is a soluble salt-forming cation. Resin acids and hydrogenated resin acids are also suitable, such as rosin, hydrogenated rosin, and resin acids and hydrogenated resin acids present in or derived from tall oil.

Further examples are described in "Surface Active Agents and Detergents" (Vol. I and II by Schwartz, Perry and Berch). A variety of such surfactants are also generally disclosed in U.S. Pat. No. 3,929,678, issued Dec. 30, 1975 to Laughlin, et al. at Column 23, line 58 through Column 29, line 23 (herein incorporated by reference).

When included therein, the laundry detergent compositions of the present invention typically comprise from about 1% to about 40%, preferably from about 3% to about 20% by weight of such anionic surfactants.

Highly preferred anionic surfactants include alkyl alkoxylated sulfate surfactants hereof are water soluble salts or acids of the formula $RO(A)_m$SO3M wherein R is an unsubstituted $C_{10}$–$C_{24}$ alkyl or hydroxyalkyl group having a $C_{10}$–$C_{24}$ alkyl component, preferably a $C_{12}$–$C_{20}$ alkyl or hydroxyalkyl, more preferably $C_{12}$–$C_{18}$ alkyl or hydroxyalkyl, A is an ethoxy or propoxy unit, m is greater than zero, typically between about 0.5 and about 6, more preferably between about 0.5 and about 3, and M is H or a cation which can be, for example, a metal cation (e.g., sodium, potassium, lithium, calcium, magnesium, etc.), ammonium or substituted-ammonium cation. Alkyl ethoxylated sulfates as well as alkyl propoxylated sulfates are contemplated herein. Specific examples of substituted ammonium cations include methyl-, dimethyl, trimethyl-ammonium cations and quaternary ammonium cations such as tetramethyl-ammonium and dimethyl piperdinium cations and those derived from alkylamines such as ethylamine, diethylamine, triethylamine, mixtures thereof, and the like. Exemplary surfactants are $C_{12}$–$C_{18}$ alkyl polyethoxylate (1.0) sulfate ($C_{12}$–$C_{18}E(1.0)M$), $C_{12}$–$C_{18}$ alkyl polyethoxylate (2.25) sulfate ($C_{12}$–$C_{18}E(2.25)M$), $C_{12}$–$C_{18}$ alkyl polyethoxylate (3.0) sulfate ($C_{12}$–$C_{18}E(3.0)M$), and $C_{12}$–$C_{18}$ alkyl polyethoxylate (4.0) sulfate ($C_{12}$–$C_{18}E(4.0)M$), wherein M is conveniently selected from sodium and potassium.

The fabric care compositions of the present invention may also contain cationic, ampholytic, zwitterionic, and semi-polar surfactants, as well as the nonionic and/or anionic surfactants other than those already described herein.

Cationic detersive surfactants suitable for use in the fabric care compositions of the present invention are those having one long-chain hydrocarbyl group. Examples of such cationic surfactants include the ammonium surfactants such as alkyltrimethylammonium halogenides, and those surfactants having the formula:

$$[R^2(OR^3)_y][R^4(OR^3)_y]_2R^5N+X-$$

wherein $R^2$ is an alkyl or alkyl benzyl group having from about 8 to about 18 carbon atoms in the alkyl chain, each $R^3$ is selected from the group consisting of —$CH_2CH_2$—, —$CH_2CH(CH_3)$—, —$CH_2CH(CH_2OH)$—, —$CH_2CH_2CH_2$—, and mixtures thereof; each $R^4$ is selected from the group consisting of $C_1$–$C_4$ alkyl, $C_1$–$C_4$ hydroxyalkyl, benzyl ring structures formed by joining the two $R^4$ groups, —$CH_2CHOH$—$CHOHCOR^6CHOHCH_2OH$ wherein $R^6$ is any hexose or hexose polymer having a molecular weight less than about 1000, and hydrogen when y is not 0; $R^5$ is the same as $R^4$ or is an alkyl chain wherein the total number of carbon atoms of $R^2$ plus $R^5$ is not more than about 18; each y is from 0 to about 10 and the sum of the y values is from 0 to about 15; and X is any compatible anion.

Quaternary ammonium surfactant suitable for the present invention has the formula (I):

Formula I

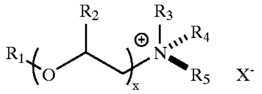

whereby R1 is a short chainlength alkyl (C6–C10) or alkylamidoalkyl of the formula (II):

Formula II

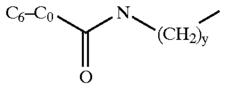

y is 2–4, preferably 3.

whereby R2 is H or a C1–C3 alkyl, whereby x is 0–4, preferably 0–2, most preferably 0, whereby R3, R4 and R5 are either the same or different and can be either a short chain alkyl (C1–C3) or alkoxylated alkyl of the formula III, whereby X_ is a counterion, preferably a halide, e.g. chloride or methylsulfate.

Formula III

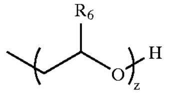

R6 is $C_1$–$C_4$ and z is 1 or 2.

Preferred quat ammonium surfactants are those as defined in formula I whereby $R_1$ is $C_8$, $C_{10}$ or mixtures thereof, x=o, $R_3$, $R_4$=$CH_3$ and $R_5$=$CH_2CH_2OH$.

Highly preferred cationic surfactants are the water-soluble quaternary ammonium compounds useful in the present composition having the formula:

$$R_1R_2R_3R_4N^+X^- \quad \text{(i)}$$

wherein $R_1$ is $C_8$–$C_{16}$ alkyl, each of $R_2$, $R_3$ and $R_4$ is independently $C_1$–$C_4$ alkyl, $C_1$–$C_4$ hydroxy alkyl, benzyl, and $-(C_2H_{40})_xH$ where x has a value from 2 to 5, and X is an anion. Not more than one of $R_2$, $R_3$ or $R_4$ should be benzyl.

The preferred alkyl chain length for $R_1$ is $C_{12}$–$C_{15}$ particularly where the alkyl group is a mixture of chain lengths derived from coconut or palm kernel fat or is derived synthetically by olefin build up or OXO alcohols synthesis. Preferred groups for $R_2R_3$ and $R_4$ are methyl and hydroxyethyl groups and the anion X may be selected from halide, methosulphate, acetate and phosphate ions. Examples of suitable quaternary ammonium compounds of formulae (i) for use herein are:

coconut trimethyl ammonium chloride or bromide;

coconut methyl dihydroxyethyl ammonium chloride or bromide;

decyl triethyl ammonium chloride;

decyl dimethyl hydroxyethyl ammonium chloride or bromide;

$C_{12-15}$ dimethyl hydroxyethyl ammonium chloride or bromide;

coconut dimethyl hydroxyethyl ammonium chloride or bromide;

myristyl trimethyl ammonium methyl sulphate;

lauryl dimethyl benzyl ammonium chloride or bromide;

lauryl dimethyl (ethenoxy)$_4$ ammonium chloride or bromide;

choline esters (compounds of formula (i) wherein $R_1$ is

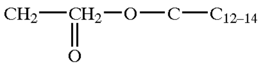 alkyl and $R_2R_3R_4$ are methyl).

di-alkyl imidazolines [compounds of formula (i)].

Other cationic surfactants useful herein are also described in U.S. Pat. No. 4,228,044, Cambre, issued Oct. 14, 1980 and in European Patent Application EP 000,224.

When included therein, the fabric care compositions of the present invention typically comprise from 0.2% to about 25%, preferably from about 1% to about 8% by weight of such cationic surfactants.

Ampholytic surfactants are also suitable for use in the fabric care compositions of the present invention. These surfactants can be broadly described as aliphatic derivatives of secondary or tertiary amines, or aliphatic derivatives of heterocyclic secondary and tertiary amines in which the aliphatic radical can be straight- or branched-chain. One of the aliphatic substituents contains at least about 8 carbon atoms, typically from about 8 to about 18 carbon atoms, and at least one contains an anionic water-solubilizing group, e.g. carboxy, sulfonate, sulfate. See U.S. Pat. No. 3,929,678 to Laughlin et al., issued Dec. 30, 1975 at column 19, lines 18–35, for examples of ampholytic surfactants. When included therein, the fabric care compositions of the present invention typically comprise from 0.2% to about 15%, preferably from about 1% to about 10% by weight of such ampholytic surfactants.

Zwitterionic surfactants are also suitable for use in fabric care compositions. These surfactants can be broadly described as derivatives of secondary and tertiary amines, derivatives of heterocyclic secondary and tertiary amines, or derivatives of quaternary ammonium, quaternary phosphonium or tertiary sulfonium compounds. See U.S. Pat. No. 3,929,678 to Laughlin et al., issued Dec. 30, 1975 at column 19, line 38 through column 22, line 48, for examples of zwitterionic surfactants.

When included therein, the fabric care compositions of the present invention typically comprise from 0.2% to about 15%, preferably from about 1% to about 10% by weight of such zwitterionic surfactants.

Semi-polar nonionic surfactants are a special category of nonionic surfactants which include water-soluble amine oxides containing one alkyl moiety of from about 10 to about 18 carbon atoms and 2 moieties selected from the group consisting of alkyl groups and hydroxyalkyl groups containing from about 1 to about 3 carbon atoms; water-soluble phosphine oxides containing one alkyl moiety of from about 10 to about 18 carbon atoms and 2 moieties selected from the group consisting of alkyl groups and hydroxyalkyl groups containing from about 1 to about 3 carbon atoms; and water-soluble sulfoxides containing one alkyl moiety of from about 10 to about 18 carbon atoms and a moiety selected from the group consisting of alkyl and hydroxyalkyl moieties of from about 1 to about 3 carbon atoms.

Semi-polar nonionic detergent surfactants include the amine oxide surfactants having the formula

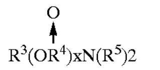

wherein $R^3$ is an alkyl, hydroxyalkyl, or alkyl phenyl group or mixtures therof containing from about 8 to about 22 carbon atoms; $R^4$ is an alkylene or hydroxyalkylene group containing from about 2 to about 3 carbon atoms or mixtures thereof; x is from 0 to about 3; and each $R^5$ is an alkyl or hydroxyalkyl group containing from about 1 to about 3 carbon atoms or a polyethylene oxide group containing from about 1 to about 3 ethylene oxide groups. The $R^5$ groups can be attached to each other, e.g., through an oxygen or nitrogen atom, to form a ring structure.

These amine oxide surfactants in particular include $C_{10}$–$C_{18}$ alkyl dimethyl amine oxides and $C_8$–$C_{12}$ alkoxy ethyl dihydroxy ethyl amine oxides. When included therein, the cleaning compositions of the present invention typically comprise from 0.2% to about 15%, preferably from about 1% to about 10% by weight of such semi-polar nonionic surfactants.

The fabric care composition of the present invention may further comprise a cosurfactant selected from the group of primary or tertiary amines. Suitable primary amines for use herein include amines according to the formula $R_1NH_2$ wherein $R_1$ is a $C_6$–$C_{12}$, preferably $C_6$–$C_{10}$ alkyl chain or $R_4X(CH_2)_n$, X is —O—,—C(O)NH— or —NH—$R_4$ is a $C_6$–$C_{12}$ alkyl chain n is between 1 to 5, preferably 3. $R_1$ alkyl chains may be straight or branched and may be interrupted with up to 12, preferably less than 5 ethylene oxide moieties. Preferred amines according to the formula herein above are n-alkyl amines. Suitable amines for use herein may be selected from 1-hexylamine, 1-octylamine, 1-decylamine and laurylamine. Other preferred primary amines include C8–C10 oxypropylamine, octyloxypropylamine, 2-ethylhexyl-oxypropylamine, lauryl amido propylamine and amido propylamine.

Suitable tertiary amines for use herein include tertiary amines having the formula $R_1R_2R_3N$ wherein R1 and R2 are $C_1$–$C_8$ alkylchains or

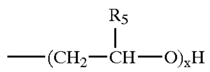

$R_3$ is either a $C_6$–$C_{12}$, preferably $C_6$–$C_{10}$ alkyl chain, or $R_3$ is $R_4X(CH_2)_n$, whereby X is —O—, —C(O)NH— or —NH—$R_4$ is a $C_4$–$C_{12}$, n is between 1 to 5, preferably 2–3. $R_5$ is H or $C_1$–$C_2$ alkyl and x is between 1 to 6. $R_3$ and $R_4$ may be linear or branched ; $R_3$ alkyl chains may be interrupted with up to 12, preferably less than 5, ethylene oxide moieties.

Preferred tertiary amines are $R_1R_2R_3N$ where R1 is a C6–C12 alkyl chain, R2 and R3 are C1–C3 alkyl or

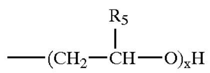

where R5 is H or CH3 and x=1–2.

Also preferred are the amidoamines of the formula:

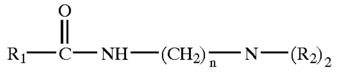

wherein $R_1$ is $C_6$–$C_{12}$ alkyl; n is 2–4,
preferably n is 3; $R_2$ and $R_3$ is $C_1$–$C_4$ Most preferred amines of the present invention include 1-octylamine, 1-hexylamine, 1-decylamine, 1-dodecylamine,C8–10oxypropylamine, N coco 1-3diaminopropane, coconutalkyldimethylamine, lauryldimethylamine, lauryl bis(hydroxyethyl)amine, coco bis(hydroxyethyl)amine, lauryl amine 2 moles propoxylated, octyl amine 2 moles propoxylated, lauryl amidopropyl-dimethylamine, C8–10 amidopropyldimethylamine and C10 amidopropyl-dimethylamine.

The most preferred amines for use in the compositions herein are 1-hexylamine, 1-octylamine, 1-decylamine, 1-dodecylamine. Especially desirable are n-dodecyldimethylamine and bishydroxyethylcoconutalkylamine and oleylamine 7 times ethoxylated, lauryl amido propylamine and cocoamido propylamine.

Bleaching Agent

Additional optional detergent ingredients that can be included in the fabric care compositions when formulated as laundry softening through-the-wash compositions of the present invention include bleaching agents such as hydrogen peroxide, PB1, PB4 and percarbonate with a particle size of 400–800 microns. These bleaching agent components can include one or more oxygen bleaching agents and, depending upon the bleaching agent chosen, one or more bleach activators. When present oxygen bleaching compounds will typically be present at levels of from about 1% to about 25%.

The bleaching agent component for use herein can be any of the bleaching agents useful for fabric care compositions including oxygen bleaches as well as others known in the art. The bleaching agent suitable for the present invention can be an activated or non-activated bleaching agent.

One category of oxygen bleaching agent that can be used encompasses percarboxylic acid bleaching agents and salts thereof. Suitable examples of this class of agents include magnesium monoperoxyphthalate hexahydrate, the magnesium salt of meta-chloro perbenzoic acid, 4-nonylamino-4-oxoperoxybutyric acid and diperoxydodecanedioic acid. Such bleaching agents are disclosed in U.S. Pat. No. 4,483,781, U.S. patent application Ser. No. 740,446, European Patent Application 0,133,354 and U.S. Pat. No. 4,412,934. Highly preferred bleaching agents also include 6-nonylamino-6-oxoperoxycaproic acid as described in U.S. Pat. 4,634,551.

Another category of bleaching agents that can be used encompasses the halogen bleaching agents. Examples of hypohalite bleaching agents, for example, include trichloro isocyanuric acid and the sodium and potassium dichloroisocyanurates and N-chloro and N-bromo alkane sulphonamides. Such materials are normally added at 0.5–10% by weight of the finished product, preferably 1–5% by weight.

The hydrogen peroxide releasing agents can be used in combination with bleach activators such as tetraacetylethylenediamine (TAED), nonanoyloxy-benzene-sulfonate (NOBS, described in U.S. Pat. No. 4,412,934), 3,5,-trimethylhexanoloxybenzenesulfonate (ISONOBS, described in EP 120,591) or pentaacetylglucose (PAG)or Phenolsulfonate ester of N-nonanoyl-6-aminocaproic acid (NACA-OBS, described in WO94/28106), which are perhydrolyzed to form a peracid as the active bleaching species, leading to improved bleaching effect. Also suitable activators are acylated citrate esters such as disclosed in Copending European Patent Application No. 91870207.7 and unsymetrical acyclic imide bleach activator of the following formula as disclosed in the Procter & Gamble co-pending patent applications U.S. Ser. No. 60/022,786 (filed Jul. 30, 1996) and No. 60/028,122 (filed Oct. 15, 1996):

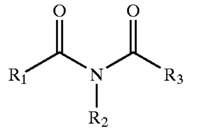

wherein $R_1$ is a $C_7$–$C_{13}$ linear or branched chain saturated or unsaturated alkyl group, $R_2$ is a $C_1$–$C_8$, linear or branched chain saturated or unsaturated alkyl group and $R_3$ is a $C_1$–$C_4$ linear or branched chain saturated or unsaturated alkyl group.

Useful bleaching agents, including peroxyacids and bleaching systems comprising bleach activators and peroxygen bleaching compounds for use in detergent compositions according to the invention are described in our co-pending applications U.S. Ser. No. 08/136,626, PCT/US95/07823, WO95/27772, WO95/27773, WO95127774 and WO95/27775.

The hydrogen peroxide may also be present by adding an enzymatic system (i.e. an enzyme and a substrate therefore) which is capable of generating hydrogen peroxide at the beginning or during the washing and/or rinsing process. Such enzymatic systems are disclosed in EP Patent Application 91202655.6 filed Oct. 9, 1991.

Metal-containing catalysts for use in bleach compositions, include cobalt-containing catalysts such as Pentaamine acetate cobalt(III) salts and manganese-containing catalysts such as those described in EPA 549 271; EPA 549 272; EPA 458 397; U.S. Pat. No. 5,246,621; EPA 458 398; U.S. Pat. Nos. 5,194,416 and 5,114,611. Bleaching composition comprising a peroxy compound, a manganese-containing bleach catalyst and a chelating agent is described in the patent application No 94870206.3.

Bleaching agents other than oxygen bleaching agents are also known in the art and can be utilized herein. One type of non-oxygen bleaching agent of particular interest includes photoactivated bleaching agents such as the sulfonated zinc and/or aluminum phthalocyanines. These materials can be deposited upon the substrate during the washing process. Upon irradiation with light, in the presence of oxygen, such as by hanging clothes out to dry in the daylight, the sulfonated zinc phthalocyanine is activated and, consequently, the substrate is bleached. Preferred zinc phthalocyanine and a photoactivated bleaching process are described in U.S. Pat. No. 4,033,718. Typically, detergent compositions will contain about 0.025% to about 1.25%, by weight, of sulfonated zinc phthalocyanine.

Builder System

The fabric care compositions when formulated as laundry softening through-the-wash compositions according to the present invention may further comprise a builder system. Any conventional builder system is suitable for use herein including aluminosilicate materials, silicates, polycarboxylates, alkyl- or alkenyl-succinic acid and fatty acids, materials such as ethylenediamine tetraacetate, diethylene triamine pentamethyleneacetate, metal ion sequestrants such as aminopolyphosphonates, particularly ethylenediamine tetramethylene phosphonic acid and diethylene triamine pentamethylenephosphonic acid. Phosphate builders can also be used herein.

Suitable builders can be an inorganic ion exchange material, commonly an inorganic hydrated aluminosilicate material, more particularly a hydrated synthetic zeolite such as hydrated zeolite A, X, B, HS or MAP. Another suitable inorganic builder material is layered silicate, e.g. SKS-6 (Hoechst). SKS-6 is a crystalline layered silicate consisting of sodium silicate ($Na_2Si_2O_5$).

Suitable polycarboxylates containing one carboxy group include lactic acid, glycolic acid and ether derivatives thereof as disclosed in Belgian Patent Nos. 831,368, 821,369 and 821,370. Polycarboxylates containing two carboxy groups include the water-soluble salts of succinic acid, malonic acid, (ethylenedioxy) diacetic acid, maleic acid, diglycollic acid, tartaric acid, tartronic acid and fumaric acid, as well as the ether carboxylates described in German Offenlegenschrift 2,446,686, and 2,446,687 and U.S. Pat. No. 3,935,257 and the sulfinyl carboxylates described in Belgian Patent No. 840,623. Polycarboxylates containing three carboxy groups include, in particular, water-soluble citrates, aconitrates and citraconates as well as succinate derivatives such as the carboxymethyloxysuccinates described in British Patent No. 1,379,241, lactoxysuccinates described in Netherlands Application 7205873, and the oxypolycarboxylate materials such as 2-oxa-1,1,3-propane tricarboxylates described in British Patent No. 1,387,447.

Polycarboxylates containing four carboxy groups include oxydisuccinates disclosed in British Patent No. 1,261,829, 1,1,2,2-ethane tetracarboxylates, 1,1,3,3-propane tetracarboxylates and 1,1,2,3-propane tetracarboxylates. Polycarboxylates containing sulfo substituents include the sulfosuccinate derivatives disclosed in British Patent Nos. 1,398,421 and 1,398,422 and in U.S. Pat. No. 3,936,448, and the sulfonated pyrolysed citrates described in British Patent No. 1,082,179, while polycarboxylates containing phosphone substituents are disclosed in British Patent No. 1,439,000.

Alicyclic and heterocyclic polycarboxylates include cyclopentane-cis,cis,cis-tetracarboxylates, cyclopentadienide pentacarboxylates, 2,3,4,5-tetrahydro-furan-cis, cis, cis-tetracarboxylates, 2,5-tetrahydro-furan -cis - dicarboxylates, 2,2,5,5-tetrahydrofuran-tetracarboxylates, 1,2,3,4,5,6-hexane-hexacarboxylates and carboxymethyl derivatives of polyhydric alcohols such as sorbitol, mannitol and xylitol. Aromatic poly-carboxylates include mellitic acid, pyromellitic acid and the phthalic acid derivatives disclosed in British Patent No. 1,425,343. Of the above, the preferred polycarboxylates are hydroxycarboxylates containing up to three carboxy groups per molecule, more particularly citrates.

Preferred builder systems for use in the present compositions include a mixture of a water-insoluble aluminosilicate builder such as zeolite A or of a layered silicate (SKS-6), and a water-soluble carboxylate chelating agent such as citric acid. Other preferred builder systems include a mixture of a water-insoluble aluminosilicate builder such as zeolite A, and a watersoluble carboxylate chelating agent such as citric acid. Preferred builder systems for use in liquid detergent compositions of the present invention are soaps and polycarboxylates.

Other builder materials that can form part of the builder system for use in granular compositions include inorganic materials such as alkali metal carbonates, bicarbonates, silicates, and organic materials such as the organic phosphonates, amino polyalkylene phosphonates and amino polycarboxylates. Other suitable water-soluble organic salts are the homo- or co-polymeric acids or their salts, in which the polycarboxylic acid comprises at least two carboxyl radicals separated from each other by not more than two carbon atoms Polymers of this type are disclosed in GB-A-1,596,756. Examples of such salts are polyacrylates of MW 2000-5000 and their copolymers with maleic anhydride, such copolymers having a molecular weight of from 20,000 to 70,000, especially about 40,000.

Detergency builder salts are normally included in amounts of from 5% to 80% by weight of the composition preferably from 10% to 70% and most usually from 30% to 60% by weight.

Chelating Agents

The fabric care compositions when formulated as laundry softening through-the-wash compositions herein may also optionally contain one or more iron and/or manganese chelating agents. Such chelating agents can be selected from the group consisting of amino carboxylates, amino phosphonates, polyfunctionally-substituted aromatic chelating agents and mixtures therein, all as hereinafter defined. Without intending to be bound by theory, it is believed that the benefit of these materials is due in part to their exceptional ability to remove iron and manganese ions from washing solutions by formation of soluble chelates.

Amino carboxylates useful as optional chelating agents include ethylenediaminetetracetates, N-hydroxyethylethylenediaminetriacetates, nitrilotriacetates, ethylenediamine tetraproprionates, triethylenetetra-aminehexacetates, diethylenetriaminepentaacetates, and ethanoldiglycines, alkali metal, ammonium, and substituted ammonium salts therein and mixtures therein.

Amino phosphonates are also suitable for use as chelating agents in the compositions of the invention when at lease low levels of total phosphorus are permitted in detergent compositions, and include ethylenediaminetetrakis (methylenephosphonates) as DEQUEST. Preferred, these amino phosphonates to not contain alkyl or alkenyl groups with more than about 6 carbon atoms.

Polyfunctionally-substituted aromatic chelating agents are also useful in the compositions herein. See U.S. Pat. No. 3,812,044, issued May 21, 1974, to Connor et al. Preferred compounds of this type in acid form are dihydroxydisulfobenzenes such as 1,2-dihydroxy-3,5-disulfobenzene.

A preferred biodegradable chelator for use herein is ethylenediamine disuccinate ("EDDS"), especially the [S,S] isomer as described in U.S. Pat. No. 4,704,233, Nov. 3, 1987, to Hartman and Perkins.

The compositions herein may also contain water-soluble methyl glycine diacetic acid (MGDA) salts (or acid form) as a chelant or cobuilder useful with, for example, insoluble builders such as zeolites, layered silicates and the like. If utilized, these chelating agents will generally comprise from about 0.1% to about 15% by weight of the fabric care compositions herein. More preferably, if utilized, the chelating agents will comprise from about 0.1% to about 3.0% by weight of such compositions.

Suds Suppressor

Another optional ingredient is a suds suppressor, exemplified by silicones, and silica-silicone mixtures. Silicones can be generally represented by alkylated polysiloxane materials while silica is normally used in finely divided forms exemplified by silica aerogels and xerogels and hydrophobic silicas of various types. These materials can be incorporated as particulates in which the suds suppressor is advantageously releasably incorporated in a water-soluble or water-dispersible, substantially non-surface-active detergent impermeable carrier. Alternatively the suds suppressor can be dissolved or dispersed in a liquid carrier and applied by spraying on to one or more of the other components.

A preferred silicone suds controlling agent is disclosed in Bartollota et al. U.S. Pat. No. 3,933,672. Other particularly useful suds suppressors are the self-emulsifying silicone suds suppressors, described in German Patent Application DTOS 2 646 126 published Apr. 28, 1977. An example of such a compound is DC-544, commercially available from Dow Coming, which is a siloxane-glycol copolymer. Especially preferred suds controlling agent are the suds suppressor system comprising a mixture of silicone oils and 2-alkyl-alcanols. Suitable 2-alkyl-alkanols are 2-butyl-octanol which are commercially available under the trade name Isofol 12 R.

Such suds suppressor system are described in Copending European Patent application N 92870174.7 filed 10 Nov. 1992.

Especially preferred silicone suds controlling agents are described in Copending European Patent application No. 92201649.8. Said compositions can comprise a silicone/silica mixture in combination with fumed nonporous silica such as Aerosil$^{R}$.

The suds suppressors described above are normally employed at levels of from 0.001% to 2% by weight of the composition, preferably from 0.01% to 1% by weight.

Method

In another aspect of the invention, there is provided a method for providing fabric care to fabrics upon domestic treatment which comprises the step of contacting the fabrics with an aqueous medium comprising a composition as defined hereinbefore. Preferably, said aqueous medium is at a temperature between 2 to 40° C., more preferably between 5 to 25° C.

In a further aspect of the invention, the composition of the invention may be applied on a substrate, such as a dryer-sheet. Accordingly, there is also provided a method for providing fabric care on treated fabrics upon domestic treatment which comprises the step of contacting the fabrics with a composition as defined hereinbefore, wherein said composition is applied on a substrate, preferably a dryer-sheet. Preferably, where the composition of the invention is applied on a dryer-sheet, the compositions are used in tumble-drying processes.

The compositions of the invention are suitable for use in any steps of the domestic treatment, that is as a pretreatment composition, as a wash additive as a composition suitable for use in the rinse-cycle of the laundry cycle or applied on a dryer-sheet. Obviously, for the purpose of the invention, multiple applications can be made such as treating the fabric with a pre-treatment composition of the invention and also thereafter with a composition of the invention suitable for use in the rinse cycle and/or suitable for use as a dryer-sheet. The compositions of the invention may also be in a spray, foam, or aerosol form which for example can be suitable for use while ironing, or applied on the surfaces of the tumble dryer.

When formulated as "softening through the wash" compositions, the process described herein comprises contacting fabrics with a laundering solution in the usual manner and exemplified hereunder. A conventional laundry method comprises treating soiled fabric with an aqueous liquid having dissolved or dispensed therein an effective amount of the laundry detergent and/or fabric care composition. The process of the invention is conveniently carried out in the course of the cleaning process. The method of cleaning is preferably carried out at 5° C. to 95° C., especially between 10° C. and 60° C. The pH of the treatment solution is preferably from 7 to 12.

EXAMPLE

The following examples are meant to exemplify compositions of the present invention, but are not necessarily meant to limit or otherwise define the scope of the invention.

In the fabric care compositions, the enzymes levels are expressed by pure enzyme by weight of the total composition and unless otherwise specified, the detergent ingredients are expressed by weight of the total compositions. The abbreviated component identifications therein have the following meanings:

| | |
|---|---|
| LAS: | Sodium linear $C_{11-13}$ alkyl benzene sulphonate. |
| CxyAS: | Sodium $C_{1x}$–$C_{1y}$ alkyl sulfate. |
| CxyEz: | $C_{1x}$–$C_{1y}$ predominantly linear primary alcohol condensed with an average of z moles of ethylene oxide. |
| DEQA: | Di-(tallow-oxy-ethyl)dimethyl ammonium chloride. |
| DEQA (2): | Di-(soft-tallowyloxyethyl)hydroxyethyl methyl ammonium methylsulfate. |
| DTDMAMS: | Ditalllow dimethyl ammonium methylsulfate. |
| SDASA: | 1:2 ratio of stearyldimethyl amine:triple-pressed stearic acid. |
| Zeolite A: | Hydrated Sodium Aluminosilicate of formula $Na_{12}(AlO_2SiO_2)_{12}.27H_2O$ having a primary particle size in the range from 0.1 to 10 micrometers (Weight expressed on an anhydrous basis). |
| Na-SKS-6: | Crystalline layered silicate of formula δ-$Na_2Si_2O_5$. |
| Citrate: | Tri-sodium citrate dihydrate of activity 86.4% with a particie size distribution between 425 and 850 micrometers. |
| Carbonate: | Anhydrous sodium carbonate with a particle size between 200 and 900 micrometers. |
| MA/AA: | Random copolymer of 4:1 acrylate/maleate, average molecular weight about 70,000–80,000. |
| PB1: | Anhydrous sodium perborate monohydrate of nominal formula $NaBO_2.H_2O_2$. |
| Percarbonate: | Anhydrous sodium percarbonate of nominal formula $2Na_2CO_3.3H_2O_2$. |
| TAED: | Tetraacetylethylenediamine. |
| DETPMP: | Diethyltriamine penta(methylene)phosphonate, marketed by Monsanto under the Trade name Dequest 2060. |
| Protease: | Proteolytic enzyme sold under the tradename Savinase, Alcalase, Durazym by Novo Nordisk NS, Maxacal, Maxapem sold by Gist-Brocades and proteases described in patents WO91/06637 and/or WO95/10591. |
| Amylase: | Amylolytic enzyme sold under the tradename Purafact Ox Am ® described in WO94/18314, WO96/05295 sold by Genencor; Termamyl ®, Fungamyl ® and Duramyl ®, all available from Novo Nordisk A/S and those described in WO95/26397. |
| Lipase: | Lipolytic enzyme sold under the tradename Lipolase, Lipolase Ultra by Novo Nordisk A/S and Lipomax by Gist-Brocades. |
| Cellulase: | Cellulytic enzyme sold under the tradename Carezyme, Celluzyme and/or Endolase by Novo Nordisk A/S. |
| CBD1: | Double CBD comprising the N-terminal CBD of *Trichoderma reesei* CBHII linked to the C-terminal CBD of CBHI via a linking region of 24 amino acid (M. Linder et al - The Journal of Biological Chemistry, Vol. 271. No. 35, issue of August, pp 21268–21272, 1996) |
| CBD2: | CBD Cellulozome from *Clostridium cellulovorans*, which is sold under the tradename Cellulose Binding Domain by Sigma, linked to a C18 alkyl quaternary weat protein derivative sold under the tradename Coltide HQS by Croda Colloids Ltd. |
| CMC: | Sodium carboxymethyl cellulose. |
| Silicone antifoam: | Polydimethylsiloxane foam controller with siloxane-oxyalkylene copolymer as dispersing agent with a ratio of said foam controller to said dispersing agent of 10:1 to 100:1. |
| Suds Suppressor: | 12% Silicone/silica, 18% stearyl alcohol, 70% starch in granular form. |
| HMWPEO: | High molecular weight polyethylene oxide. |

Example 1

The following granular fabric detergent compositions which provide "softening through the wash" capability were prepared according to the present invention:

| | I | II |
|---|---|---|
| C45AS | — | 10.0 |
| LAS | 7.6 | — |
| C68AS | 1.3 | — |
| C25E7 | 4.0 | — |
| C25E3 | — | 5.0 |
| Coco-alkyl-dimethyl hydroxyethyl ammonium chloride | 1.4 | 1.0 |
| Citrate | 5.0 | 3.0 |
| Na-SKS-6 | — | 11.0 |
| Zeolite A | 15.0 | 15.0 |
| MA/AA | 4.0 | 4.0 |
| DETPMP | 0.4 | 0.4 |
| PB1 | 15.0 | — |
| Percarbonate | — | 15.0 |
| TAED | 5.0 | 5.0 |
| Smectite clay | 10.0 | 10.0 |
| HMWPEO | — | 0.1 |
| Protease | 0.02 | 0.01 |
| Lipase | 0.002 | 0.01 |
| Amylase | 0.03 | 0.005 |
| Cellulase | 0.001 | 0.0005 |
| CBD1 | — | 2.0 |
| CBD2 | 0.2 | — |
| Silicate | 3.0 | 5.0 |
| Carbonate | 10.0 | 10.0 |
| Suds suppressor | 1.0 | 4.0 |
| CMC | 0.2 | 0.1 |
| Water/minors | Up to 100% | |

Example 2

The following rinse added fabric softener compositions were prepared according to the present invention:

| | I | II | III |
|---|---|---|---|
| CBD1 | — | 2.0 | 0.5 |
| CBD2 | 0.2 | — | 0.05 |
| DEQA (2) | 20.0 | 20.0 | 20.0 |
| Cellulase | 0.001 | 0.001 | 0.001 |
| HCL | 0.03 | 0.03 | 0.03 |
| Antifoam agent | 0.01 | 0.01 | 0.01 |
| Blue dye | 25 ppm | 25 ppm | 25 ppm |
| $CaCl_2$ | 0.20 | 0.20 | 0.20 |
| Perfume | 0.90 | 0.90 | 0.90 |
| Miscellaneous and water | | Up to 100% | |

Example 3

The following fabric softener and dryer added fabric conditioner compositions were prepared according to the present invention:

| | I | II | III | IV | V |
|---|---|---|---|---|---|
| DEQA | 2.6 | 19.0 | — | — | — |
| DEQA (2) | — | — | — | — | 51.8 |
| DTMAMS | — | — | — | 26.0 | — |
| SDASA | — | — | 70.0 | 42.0 | 40.2 |
| Stearic acid of IV = 0 | 0.3 | — | — | — | — |
| Neodol 45-13 | — | — | 13.0 | — | — |
| Hydrochloride acid | 0.02 | 0.02 | — | — | — |
| Ethanol | — | — | 1.0 | — | — |
| Cellulase | 0.0001 | 0.001 | 0.0005 | 0.005 | 0.0003 |
| CBD1 | — | 1.0 | 1.0 | — | 5.0 |
| CBD2 | 0.2 | — | — | 0.2 | — |
| Perfume | 1.0 | 1.0 | 0.75 | 1.0 | 1.5 |

-continued

| | I | II | III | IV | V |
|---|---|---|---|---|---|
| Glycoperse S-20 | — | — | — | — | 15.4 |
| Glycerol monostearate | — | — | — | 26.0 | — |
| Digeranyl Succinate | — | — | 0.38 | — | — |
| Silicone antifoam | 0.01 | 0.01 | — | — | — |
| Electrolyte | — | 0.1 | — | — | — |
| Clay | — | — | — | 3.0 | — |
| Dye | 10 ppm | 25 ppm | 0.01 | — | — |
| Water and minors | 100% | 100% | — | — | — |

Example 4

The following pre- or post treatment compositions were prepared in accord with the present invention:

| | I | II | III |
|---|---|---|---|
| CBD1 | 2.0 | 1.0 | — |
| CBD2 | — | — | 0.4 |
| DEQA (2) | — | 20.0 | 20.0 |
| Cellulase | 0.002 | 0.001 | 0.001 |
| HCL | — | 0.03 | 0.03 |
| Antifoam agent | — | 0.01 | 0.01 |
| Blue dye | 25 ppm | 25 ppm | 25 ppm |
| $CaCl_2$ | — | 0.20 | 0.20 |
| Perfume | 0.90 | 0.90 | 0.90 |
| Water/minors | | Up to 100% | |

What is claimed is:

1. A fabric softening protein hybrid comprising an amino acid sequence comprising a cellulose binding domain linked to a fabric softening protein;

wherein said fabric softening protein is linked to said amino acid sequence comprising a cellulose binding domain, via a non-amino acid linking region;

wherein the cellulose binding domain is selected from the group consisting of CBD Cellulozome from *Clostridium cellulovorans*, CBD E3 from *Thermonospora fusca*, CBD-dimer from *Clostridium stecorarium* XynA, CBD from *Bacillus agaradherens*, and combinations thereof;

further wherein said non-amino linking region is a polymer selected from the group consisting of polyethylene glycol derivatives, nucleophilic polyethylene glycol derivatives, carboxyl polyethylene glycol derivatives, electrophilically activated polyethylene glycol derivatives, sulfhydryl-selective polyethylene glycol derivatives, heterofunctional polyethylene glycol derivatives, biotin polyethylene glycol derivatives, vinyl polyethylene glycol derivatives, silane polyethylene glycol derivatives, phospholipid polyethylene glycol derivatives, 1-ethyl-3-(3-dimethylaminopropyl) carbodiimide, N-ethyl-5-phenylisoaxolium-3-sulphonate, 1-cyclohexyl-3(2-morpholinoethyl) carbodide metho-p-toluene sulphonate, N-ethoxycarbonyl-2-ethoxy 1,2, dihydroquinoline, glutaraldehyde and mixtures thereof; and further wherein said fabric softening protein is selected from the group consisting of: hydrolases, lyases, oxidoreductases, ligases, transferases, isomerases, cellulases, xylanases, mannanases, arabinofuranosidases, acetylesterases, chitinases, polyamino acid resin solutions, $C_{18}$ alkyl quaternary wheat protein derivatives and combinations thereof.

2. A fabric care composition comprising the fabric softening protein hybrid according to claim 1.

3. A fabric softening protein hybrid according to claim 1 wherein the amino acid sequence comprising a cellulose binding domain is selected from CBD Cellulozome from *Clostridium cellulovorans*.

4. A fabric care composition according to claim 2 further comprising another fabric care ingredient.

5. A fabric care composition according to claim 2 further comprising a fabric care ingredient wherein said fabric care ingredient is selected from the group consisting of a cationic surfactant comprising two long alkyl chain lengths, a clay, a transferase and/or mixtures thereof.

6. A method comprising the step of contacting a fabric with a fabric care composition according to claim 2 to provide fabric softness, anti-wrinkle properties, anti-bobbling properties, anti-shrinkage properties, static control, colour appearance and fabric anti-wear properties and to provide, refurbish or restore tensile strength.

* * * * *